United States Patent [19]

Fukunaga et al.

[11] Patent Number: 5,736,384
[45] Date of Patent: Apr. 7, 1998

[54] THERMOSTABLE XYLANASE

[75] Inventors: Nobuyuki Fukunaga; Yuji Iwasaki, both of Tokyo; Satoko Kono, Saitama; Yukio Kita; Yoshiya Izumi, both of Tokyo, all of Japan

[73] Assignee: New Oji Paper Company Ltd., Tokyo, Japan

[21] Appl. No.: 575,964

[22] Filed: Dec. 20, 1995

[30] Foreign Application Priority Data

Dec. 21, 1994 [JP] Japan .................................. 6-318450
Nov. 30, 1995 [JP] Japan .................................. 7-313081

[51] Int. Cl.$^6$ .................. C12N 9/24; C12S 3/00; C12S 3/08
[52] U.S. Cl. .................. 435/278; 435/200; 435/277
[58] Field of Search .................. 435/200, 277, 435/278

[56] References Cited

U.S. PATENT DOCUMENTS 5,369,024 11/1994 Jeffries et al. .................. 435/200

FOREIGN PATENT DOCUMENTS

92/13942 8/1992 WIPO.

OTHER PUBLICATIONS

Okazaki et al., Agric. Biol. Chem. 49:2033–2039, 1985.

Kang et al., Korean J. Appl. Microbiol. Bioeng. 14:447–453, 1986.

Ball et al., Proc. 8th Intl. Symposium on Wood and Pulping Chemistry, Jun. 6–9, 1995, Helsinki, Finland, pp. 395–400, 1995.

Primary Examiner—Robert A. Wax
Assistant Examiner—Eric Grimes
Attorney, Agent, or Firm—Fish & Richardson, P.C.

[57] ABSTRACT

The invention relates to a thermostable xylanase selected from xylanase XP1 having a molecular weight of about 22,500, an isoelectric point at around 8.1 and an optimum temperature for reaction of 70° C. or xylanase XP2 having a molecular weight of about 32,000, an isoelectric point at around 8.5 and an optimum temperature for reaction of 80° C., a gene encoding for the thermostable xylanase, a method for producing the xylanase, applications of the xylanase, a bleaching agent containing the xylanase as an active ingredient, a method for bleaching pulp by using the bleaching agent and Bacillus sp. 2113 and Bacillus sp. 208 both having an ability to produce a thermostable xylanase.

6 Claims, 8 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

-continued

```
( i ) SEQUENCE CHARACTERISTICS:
        ( A ) LENGTH: 211 amino acids
        ( B ) TYPE: amino acid
        ( C ) STRANDEDNESS: Not Relevant
        ( D ) TOPOLOGY: linear ( i i ) MOLECULE TYPE: protein ( v i ) ORIGINAL SOURCE:
        ( A ) ORGANISM: Bacillus sp.
        ( B ) STRAIN: 2113

( i x ) FEATURE:
        ( D ) OTHER INFORMATION: 1-23 S sig peptide.
              24-211 S mat peptide.

( x i ) SEQUENCE DESCRIPTION: SEQ ID NO:1:
```

| Met | Ile | Lys | Ser | Lys | Lys | Phe | Leu | Thr | Val | Cys | Ile | Ala | Ala | Leu |
|---|---|---|---|---|---|---|---|---|---|---|---|---|---|---|
| 1 |   |   |   | 5 |   |   |   |   | 10 |   |   |   |   | 15 |

| Met | Ser | Phe | Ser | Leu | Phe | Ala | Ala | Thr | Ser | Asn | Ala | Ala | Thr | Asp | Tyr |
|---|---|---|---|---|---|---|---|---|---|---|---|---|---|---|---|
|   |   |   | 20 |   |   |   |   | 25 |   |   |   |   |   | 30 |   |

| Trp | Gln | Tyr | Trp | Thr | Asp | Gly | Gly | Thr | Val | Asn | Ala | Thr | Asn | Gly |
|---|---|---|---|---|---|---|---|---|---|---|---|---|---|---|
|   |   | 35 |   |   |   |   | 40 |   |   |   |   | 45 |   |   |

| Ser | Gly | Gly | Asn | Tyr | Ser | Val | Thr | Trp | Ser | Asn | Val | Gly | Asn | Phe | Val |
|---|---|---|---|---|---|---|---|---|---|---|---|---|---|---|---|
|   | 50 |   |   |   |   | 55 |   |   |   |   | 60 |   |   |   |   |

| Val | Gly | Lys | Gly | Trp | Gly | Thr | Gly | Ser | Pro | Thr | Arg | Thr | Val | Asn | Tyr |
|---|---|---|---|---|---|---|---|---|---|---|---|---|---|---|---|
| 65 |   |   |   |   | 70 |   |   |   |   | 75 |   |   |   |   | 80 |

| Asn | Ala | Gly | Val | Trp | Ala | Pro | Ser | Gly | Asn | Gly | Tyr | Leu | Thr | Leu | Tyr |
|---|---|---|---|---|---|---|---|---|---|---|---|---|---|---|---|
|   |   |   |   | 85 |   |   |   |   | 90 |   |   |   |   | 95 |   |

| Gly | Trp | Thr | Arg | Asn | Ser | Leu | Ile | Glu | Tyr | Tyr | Val | Val | Asp | Ser | Trp |
|---|---|---|---|---|---|---|---|---|---|---|---|---|---|---|---|
|   |   |   | 100 |   |   |   |   | 105 |   |   |   |   | 110 |   |   |

| Gly | Thr | Tyr | Arg | Pro | Thr | Gly | Thr | Tyr | Lys | Gly | Thr | Val | Thr | Ser | Asp |
|---|---|---|---|---|---|---|---|---|---|---|---|---|---|---|---|
|   |   | 115 |   |   |   |   | 120 |   |   |   |   | 125 |   |   |   |

| Gly | Gly | Thr | Tyr | Asp | Ile | Tyr | Thr | Thr | Met | Arg | Tyr | Asn | Ala | Pro | Ser |
|---|---|---|---|---|---|---|---|---|---|---|---|---|---|---|---|
|   | 130 |   |   |   |   | 135 |   |   |   |   | 140 |   |   |   |   |

| Ile | Asp | Gly | Thr | Gln | Thr | Phe | Pro | Gln | Tyr | Trp | Ser | Val | Arg | Gln | Ser |
|---|---|---|---|---|---|---|---|---|---|---|---|---|---|---|---|
| 145 |   |   |   |   | 150 |   |   |   |   | 155 |   |   |   |   | 160 |

| Lys | Arg | Pro | Thr | Gly | Ser | Asn | Val | Ser | Ile | Thr | Phe | Ser | Asn | His | Val |
|---|---|---|---|---|---|---|---|---|---|---|---|---|---|---|---|
|   |   |   |   | 165 |   |   |   |   | 170 |   |   |   |   | 175 |   |

| Asn | Ala | Trp | Arg | Asn | Ala | Gly | Met | Asn | Leu | Gly | Ser | Ser | Trp | Ala | Tyr |
|---|---|---|---|---|---|---|---|---|---|---|---|---|---|---|---|
|   |   |   | 180 |   |   |   |   | 185 |   |   |   |   | 190 |   |   |

| Gln | Val | Leu | Ala | Val | Glu | Gly | Tyr | Gln | Ser | Ser | Gly | Ser | Ala | Asn | Val |
|---|---|---|---|---|---|---|---|---|---|---|---|---|---|---|---|
|   |   | 195 |   |   |   |   | 200 |   |   |   |   | 205 |   |   |   |

| Thr | Val | Trp |
|---|---|---|
|   |   | 210 |

```
( 2 ) INFORMATION FOR SEQ ID NO:2:

( i ) SEQUENCE CHARACTERISTICS:
            ( A ) LENGTH: 1207 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Bacillus sp.
            ( B ) STRAIN: 2113

( i x ) FEATURE:
            ( A ) NAME/KEY: P CDS
            ( B ) LOCATION: 379...1029
            ( C ) IDENTIFICATION METHOD: by experiment
            ( D ) OTHER INFORMATION:
```

( x i ) SEQUENCE DESCRIPTION: SEQ ID NO:2:

```
TCTTGATAAT CAGAAAATTA ACATATGGGG GGAACCCTTT GGGACCGTAC ATGTCGATGA      60
AATTGGTGTT CAATTAACCT TAGAAAGATG GACAGGAAAT GGGTGAAAGT GCATAGCGGT     120
TCGAACACAA CCGTCCAATG TTACGGAACC CGTTATAACC TCGGTTCCTC GACGGTTTCT     180
ATGCATTTAA AAGTATTAAA AAAATGGGGT AAAATCTTTA ATTTGTTAAG TTGTTGTGTA     240
TACGCTTACA TTCTATAATT TACTAAAAAG GAGGTGAAAG TAAGAAGTTC GCGGAAGATC     300
CTGACACAGG ATAAGTTATG AACTTCAACG AGAACAACC GACAAGCAGG TAGTGTGCAG      360
GCAAGCAGTA ATCAAAATT TTTTAGGAGG TAAATTATGA TTAAGTCTAA AAAGAAATTT      420
TTGACGGTAT GTATTGCAGC ATTAATGAGT TTTAGCTTGT TTGCAGCAAC CTCAAATGCA     480
GCGACAGACT ATTGGCAATA TTGGACCGAT GGCGGCGGGA CAGTAAATGC TACCAATGGA     540
TCCGGCGGCA ATTACAGTGT TACATGGAGC AATGTCGGGA ATTTGTTGT CGGTAAAGGC      600
TGGGGAACCG GATCGCCAAC TAGAACGGTG AACTACAATG CCGGCGTCTG GGCGCCGTCC     660
GGCAATGGGT ATTTGACTCT CTATGGGTGG ACGAGAAACT CGCTCATCGA ATATTATGTC     720
GTGGACAGTT GGGGCACTTA TAGACCTACT GGAACGTATA AAGGCACCGT GACCAGTGAT     780
GGGGGCACCT ATGACATCTA TACGACGATG AGATACAACG CACCTTCCAT TGACGGTACA     840
CAAACTTTCC CCCAATACTG GAGTGTCCGT CAGTCGAAGA GACCGACCGG AAGCAACGTC     900
TCTATCACTT TTAGCAACCA CGTTAACGCA TGGAGAAATG CAGGCATGAA TCTGGGAAGC     960
AGTTGGGCTT ACCAGGTGTT GGCAGTAGAA GGGTATCAAA GTAGCGGGAG CGCTAACGTA    1020
ACGGTGTGGT AACAGGTCAA CTGCAAACAG GGCAACTAGA CCGTTCCGG AATATTGAGA     1080
AAGTCTTTTA ATCATTGATA TTGCTAAGGC CTGCCGGTCT CACAGCCGGC GGCCTTATAT    1140
ATTTCAACAA AAGATATTAT GGAGGAAACC GATTCCTTTT AAAGGAGAGC TACCCATGAG    1200
AAAGCTG                                                             1207
```

( 2 ) INFORMATION FOR SEQ ID NO:3:

( i ) SEQUENCE CHARACTERISTICS:
( A ) LENGTH: 10 amino acids
( B ) TYPE: amino acid
( C ) STRANDEDNESS: Not Relevant
( D ) TOPOLOGY: linear ( i i ) MOLECULE TYPE: peptide ( v i ) ORIGINAL SOURCE:
( A ) ORGANISM: Bacillus sp.
( B ) STRAIN: 2113

( x i ) SEQUENCE DESCRIPTION: SEQ ID NO:3:

```
Ala Thr Asp Tyr Trp Gln Tyr Trp Thr Asp
 1               5                   10
```

THERMOSTABLE XYLANASE

FIELD OF THE INVENTION

The present invention relates to novel thermostable xylanases, methods for producing the same, applications of the same, thermostable xylanase genes and microorganisms producing a thermostable xylanase.

BACKGROUND ART

Xylanase is an enzyme which degrades xylan. It is a useful enzyme employed in a pretreatment process for the bleaching of pulp in paper manufacturing or in the manufacturing of functional xyloligosaccharides.

Since Viikari et al. reported that the bleaching effect on kraft pulp is improved with xylanase [Abstract of the Presentations for the 3rd International Conference on Biotechnology in the Pulp and Paper Industry (1986), p. 67], xylanase has begun to attract attention in the paper pulp industry. In the process of pulp manufacturing, there are many steps, such as kraft digesting and bleaching, which are carried out under high temperature conditions. Accordingly, in order to efficiently use xylanase in these steps, a highly thermostable xylanase is desired. Since the use of a thermostable xylanase enables an enzyme reaction at a high temperature, facilities and energy required for cooling can be reduced. Furthermore, the contamination during the enzymatic treatment can also be prevented.

On the other hand, it is obvious that a microorganism which produces a high amount of an enzyme is advantageous from the view point of cost reduction in enzyme production.

Therefore, a highly thermostable xylanase and a microorganism which produces a high amount of this enzyme are desired.

With respect to microorganisms producing a xylanase, a number of microorganisms such as filamentous fungi belonging to the genera Aspergillus, Trichoderma, Aureobasidium and *Schizophyllum commune* and bacteria belonging to the genera Bacillus, Clostridium and Streptomyces according to a review of xylanase (Wong et al., Microbiological Reviews, Sept., 305, 1988) and the like are known. The reaction pH of the xylanases from these microorganisms is acidic to neutral and their reaction temperature ranges from 40° to 80° C. There are also known microorganisms producing an alkali xylanase which has an activity in the alkaline side. For example, microorganisms belonging to the genus Bacillus (Honda et al., System. Appl. Microbiol., 8, 152, 1986; Okazaki et al., Appl. Microbiol. and Biotechnol., 19, 335, 1984), the genus Aeromonas (Ohkoshi et al., Agric. Biol. Chem., 49, 3037, 1985) and the genus Streptomyces (Vyas et al., Biotechnol. Let., 12, 225, 1990) are known.

Among these xylanase-producing microorganisms, a number of filamentous fungi also produce cellulase as well as xylanase. Therefore, if used in pulp and paper manufacturing processes, such cellulase would cause various problems such as decrease in pulp yield or paper strength. Furthermore, filamentous fungi require a longer cultivation period than bacteria. On the other hand, the xylanase productivity of those bacteria is rather low.

Recently, Viikari et al. reported that, using alkalitolerant *Bacillus circulans* VTT-E-87305 strain, they obtained the highest xylanase activity (400 U/ml) within two days at pH 8–8.5 at 30° C. (Appl. Microbiol. Biotechnol., 37, 470, 1992). However, the thermostability of this xylanase is not clear. In addition, since the cultivation temperature is as low as 30° C., it is difficult to use this enzyme for an enzyme reaction at a high temperature.

On the other hand, with respect to the purification of a thermostable xylanase produced by a microorganism belonging to the genus Bacillus, there have been reported W1-I thermostable xylanase having a molecular weight of 21,500, an isoelectric point at 8.5, an optimum pH for reaction of 6.0 and an optimum temperature for reaction of 65° C. and W2-I thermostable xylanase having a molecular weight of 22,500, an isoelectric point at 8.3, an optimum pH for reaction of 6.0 and an optimum temperature for reaction of 65° C. derived from basophilic, thermophilic Bacillus W-1 and W-2, respectively (Okazaki et al., Agric. Biol. Chem., 49, 2033, 1985).

With respect to *Bacillus stearothermophilus* which is known as a thermophilic Bacillus, T. Nanmori et al. reported the purification and production of a thermostable xylanase having a molecular weight of 39,500, an isoelectric point at 5.1, an optimum pH for reaction of 7.0 and an optimum temperature for reaction of 60° C. from a culture filtrate of Strain 21 (J. Bacteriol., 172, 6669, 1990). However, the amount of activity for two days at 55° C. is only 1.96 U/ml.

In addition, with respect to applications of xylanase, there have been reported attempts to reduce bleaching chemicals and AOX (adsorbable organic halogen compounds, especially organic chlorides) by treating pulp with xylanase (e.g., Japanese Unexamined Patent Publications No. 2-210085, No. 2-210086, No. 2-221482, No. 2-264087, No. 2-293486, No. 3-40887 and No. 3-505785; L. S. Pederson et al., Production of Bleached Chemical Pulp in the Future International Pulp Bleaching Conference, Vol. 2, 107, 1991; KAMI PARUPU GIJUTU TAIMUZU (Paper Pulp Technology Times) issued on May 20, 1992; S. Hogman et al., Biotechnology in Pulp and Paper Industry, Uni Publishers Co., Ltd., p. 107, 1992; and Viikari et al., Biotechnology in Pulp and Paper Industry, Uni Publishers Co., Ltd., p. 101, 1992).

In these attempts, however, while a high temperature treatment at 40°–100° C. is necessary for the bleaching step in the pulp and paper manufacturing processes, a non-thermostable enzyme is often used in the bleaching process. For this enzymatic treatment, pulp must be cooled to the optimum temperature for the enzyme reaction and then heated for the subsequent step, which requires enormous energy.

Because of high temperature cultivation, this enzyme can be produced without cooling facilities or with saving of cooling water, and yet with reducing the possibility of pulp contamination with various microorganisms. It is possible to manufacture the enzyme at a low cost. Accordingly, a thermostable xylanase is desired.

In addition, it is also desired to obtain a thermostable xylanase in large quantity by expressing the gene by recombinant DNA techniques and a gene coding for the xylanase.

A number of papers have been reported on xylanase genes. For example, there are genes derived from bacteria, such as *Bacillus circulans* [Yang R. C. A. et al., Nucleic Acids Res. 16 :7187–7187 (1988)], *Bacillus subtilis* [Paice M. G. et al., Arch. Microbiol. 144:201–206 (1986)], *Pseudomonas fluorescens* [Kellett L. E. et al., Biochem. J. 272:369–376 (1990)] and *Ruminococcus flavefaciens* [Zhang J. X. et al., Mol. Microbiol. 6:1013–1023 (1992)], and genes derived from fungi, such as *Clostridium acetobutylicum* [Zappe et al., Nucleic Acids Res. 18:2179–2179 (1990], *Aspergillus awamori* [Ito K. et al., Biosci. Biotechnol. Biochem. 56:1338–1340 (1992)] and *Streptomyces liv-*

*idans* [Shareck F. et al., Gene 107:75–82 (1991)]. However, it is not clear whether those enzymes produced by the transformants obtained by using these genes are suitable for bleaching or not.

SUMMARY OF THE INVENTION

It is an object of the present invention to provide novel thermostable xylanases, methods for producing the same, applications of the same, thermostable xylanase genes and microorganisms producing a thermostable xylanase.

The present inventors have made extensive and intensive researches toward the solution of the above-mentioned assignment. As a result of keen and wide screening for microorganisms which produce a thermostable xylanase highly, the inventors have found thermostable xylanase-producing microorganisms in a soil at Shinonome, Koutou-ku, Tokyo, Japan. The inventors have found thermostable xylanases XP1 and XP2 having excellent thermostable properties in a culture of these microorganisms, cloned genes coding for these thermostable xylanases and succeeded in highly expressing the genes. Thus, the present invention has been achieved.

The present invention relates to a thermostable xylanase selected from thermostable xylanase XP1 or XP2 having the following physicochemical properties:

(1) Thermostable xylanase XP1 (hereinafter referred to as "XP1") having the following physicochemical properties:
  i. Action: hydrolyzing the 1,4-β-D-xyloside bond of xylan to thereby produce reducing sugars of xylo-oligosaccharides.
  ii. Substrate specificity: acting on prepared xylans including birch xylan and oat spelt xylan, as well as xylan-containing materials including hardwood kraft pulp and oat spelt bran.
  iii. Optimum pH and stable pH ranges: optimum pH for reaction ranging from 5 to 8 and the pH at which said xylanase is stable ranging from 3 to 9.
  iv. Appropriate temperature range for action: 50° to 80° C.
  v. Thermostability: retaining about 90% or more enzyme activity after a 30 min treatment at 50° C. and exhibiting a residual activity of about 50% or more even after a 30 min treatment at 60° C.
  vi. Isoelectric point: around 8.1.
  vii. Molecular weight: approximately 22,500 as determined by SDS polyacrylamide gel electrophoresis.
  viii. Inhibition: weakly inhibited by iodoacetic acid and EDTA and strongly inhibited by $Hg^{2+}$ and SDS.

2) Thermostable xylanase XP2 (hereinafter referred to as "XP2") having the following physicochemical properties:
  i. Action: hydrolyzing the 1,4-β-D-xyloside bond of xylan to thereby produce reducing sugars of xylose and xylooligosaccharides.
  ii. Substrate specificity: acting on prepared xylans including birch xylan and oat spelt xylan, as well as xylan-containing materials including hardwood kraft pulp and oat spelt bran.
  iii. Optimum pH and stable pH ranges: optimum pH for reaction ranging from 5 to 8 and the pH at which said xylanase is stable ranging from 4.5 to 9.
  iv. Appropriate temperature range for action: 60° to 90° C.
  v. Thermostability: exhibiting a residual activity of about 90% or more after a 30 min treatment at 70° C.
  vi. Isoelectric point: around 8.5.
  vii. Molecular weight: approximately 32,000 as determined by SDS polyacrylamide gel electrophoresis.
  viii. Inhibition: weakly inhibited by $Mn^{2+}$, $Co^{2+}$, $Cu^{2+}$, EDTA and iodoacetic acid and strongly inhibited by $Hg^{2+}$ and SDS.

The present invention also relates to a method for producing the above-mentioned thermostable xylanase, comprising culturing on a medium a microorganism belonging to the genus Bacillus which produces the thermostable xylanase and subsequently recovering the thermostable xylanase from the resultant culture. Specific examples of the microorganism include *Bacillus sp.* 2113 and *Bacillus sp.* 208.

The present invention further relates to Bacillus sp. 2113 or *Bacillus sp.* 208 having an ability to produce thermostable xylanase.

The present invention further relates to a thermostable xylanase gene which contains a nucleotide sequence substantially coding for the amino acid sequence represented by SEQ ID NO: 1 or contains substantially the nucleotide sequence represented by SEQ ID NO: 2.

The term "substantially" used here means that the amino acid or nucleotide sequence may contain changes such as deletion, substitution or addition, as long as the resultant peptide has a thermostable xylanase activity or as long as the nucleotide sequence encodes for a thermostable xylanase.

The present invention also relates to a thermostable xylanase selected from recombinant thermostable xylanase XP1 or XP2 having the following physiochemical properties:

(1) Recombinant thermostable xylanase XP1 having the following physicochemical properties:
  i. Action: hydrolyzing the 1,4-β-D-xyloside bond of xylan to thereby produce reducing sugars of xylo-oligosaccharides.
  ii. Substrate specificity: acting on prepared xylans including birch xylan and oat spelt xylan, as well as xylan-containing materials including hardwood kraft pulp and oat spelt bran.
  iii. Optimum pH and stable pH ranges: optimum pH for reaction ranging from 5 to 8 and the pH at which said xylanase is stable ranging from 3 to 9.
  iv. Appropriate temperature range for action: 50° to 80° C.
  v. Thermostability: retaining about 90% or more enzyme activity after a 30 min treatment at 50° C. and exhibiting a residual activity of about 50% or more even after a 30 min treatment at 60° C.
  vi. Isoelectric point: around 8.1.
  vii. Molecular weight: approximately 22,500 as determined by SDS polyacrylamide gel electrophoresis.
  viii. Inhibition: weakly inhibited by iodoacetic acid and EDTA and strongly inhibited by $Hg^{2+}$ and SDS.

(2) Recombinant thermostable xylanase XP2 having the following physicochemical properties:
  i. Action: hydrolyzing the 1,4-β-D-xyloside bond of xylan to thereby produce reducing sugars of xylose and xylooligosaccharides.
  ii. Substrate specificity: acting on prepared xylans including birch xylan and oat spelt xylan, as well as xylan-containing materials including hardwood kraft pulp and oat spelt bran.
  iii. Optimum pH and stable pH ranges: optimum pH for reaction ranging from 5 to 8 and the pH at which said xylanase is stable ranging from 4.5 to 9.
  iv. Appropriate temperature range for action: 60° to 90° C.

v. Thermostability: exhibiting a residual activity of about 90% or more after a 30 min treatment at 70° C.
vi. Isoelectric point: around 8.5.
vii. Molecular weight: approximately 32,000 as determined by SDS polyacrylamide gel electrophoresis.
viii. Inhibition: weakly inhibited by $Mn^{2+}$, $Co^{2+}$, $Cu^{2+}$, EDTA and iodoacetic acid and strongly inhibited by $Hg^{2+}$ and SDS.

The present invention further relates to a recombinant thermostable xylanase substantially containing the amino acid sequence represented by SEQ ID NO: 1.

The present invention also relates to a recombinant vector containing the above-mentioned thermostable xylanase gene.

The present invention further relates to a transformant transformed with the above-mentioned recombinant vector.

The present invention further relates to a method for producing a recombinant thermostable xylanase, comprising culturing the above-mentioned transformant on a medium and subsequently recovering a thermostable xylanase from the resultant culture.

The present invention further relates to a bleaching agent containing, as an active ingredient, (i) a microorganism belonging to the genus Bacillus which produces the above-mentioned thermostable xylanase or a culture obtained by culturing the above-mentioned transformant on a medium; or (ii) thermostable xylanase XP1 or recombinant thermostable xylanase XP1 and/or thermostable xylanase XP2 or recombinant thermostable xylanase XP2 having the following physicochemical properties:

(1) Thermostable xylanase XP1 or recombinant thermostable xylanase XP1 having the following physicochemical properties:
  i. Action: hydrolyzing the 1,4-β-D-xyloside bond of xylan to thereby produce reducing sugars of xylooligosaccharides.
  ii. Substrate specificity: acting on prepared xylans including birch xylan and oat spelt xylan, as well as xylan-containing materials including hardwood kraft pulp and oat spelt bran.
  iii. Optimum pH and stable pH ranges: optimum pH for reaction ranging from 5 to 8 and the pH at which said xylanase is stable ranging from 3 to 9.
  iv. Appropriate temperature range for action: 50° to 80° C.
  v. Thermostability: retaining about 90% or more enzyme activity after a 30 min treatment at 50° C. and exhibiting a residual activity of about 50% or more even after a 30 min treatment at 60° C.
  vi. Isoelectric point: around 8.1.
  vii. Molecular weight: approximately 22,500 as determined by SDS polyacrylamide gel electrophoresis.
  viii. Inhibition: weakly inhibited by iodoacetic acid and EDTA and strongly inhibited by $Hg^{2+}$ and SDS.

(2) Thermostable xylanase XP2 or recombinant thermostable xylanase XP2 having the following physicochemical properties:
  i. Action: hydrolyzing the 1,4-β-D-xyloside bond of xylan to thereby produce reducing sugars of xylose and xylooligosaccharides.
  ii. Substrate specificity: acting on prepared xylans including birch xylan and oat spelt xylan, as well as xylan-containing materials including hardwood kraft pulp and oat spelt bran.
  iii. Optimum pH and stable pH ranges: optimum pH for reaction ranging from 5 to 8 and the pH at which said xylanase is stable ranging from 4.5 to 9.
  iv. Appropriate temperature range for action: 60° to 90° C.
  v. Thermostability: exhibiting a residual activity of about 90% or more after a 30 min treatment at 70° C.
  vi. Isoelectric point: around 8.5.
  vii. Molecular weight: approximately 32,000 as determined by SDS polyacrylamide gel electrophoresis.
  viii. Inhibition: weakly inhibited by $Mn^{2+}$, $Co^{2+}$, $Cu^{2+}$, EDTA and iodoacetic acid and strongly inhibited by $Hg^{2+}$ and SDS.

The present invention further relates to a method for bleaching pulp, comprising treating pulp with the above-mentioned bleaching agent.

The present invention also relates to a method for bleaching pulp, comprising carrying out a chemical bleaching and/or an alkali extraction before, after or during the treatment of pulp with the above-mentioned bleaching agent.

DETAILED DESCRIPTION OF THE INVENTION

Now, the present invention will be described below in detail.

(1) Physicochemical Properties of the Enzymes

First, the physicochemical properties of thermostable xylanases XP1 and XP2 of the present invention are as follows.

i. Action

To 5 ml of 1% birch xylan (Sigma) solution (pH 7.0, in 40 mM sodium phosphate buffer), 10 U of each of XP1 and XP2 was added and reacted at 60° C. After a certain reaction period, the reaction was terminated by boiling and 10 μl of the reaction mixture was subjected to thin-layer chromatography using HPTLC Kieselgel 60 $F_{254}$ (Merk) as a thin layer and a mixture of n-butanol, acetic acid and water (10:5:1) as a developer. The coloring was carried out by spraying a diphenylamine-aniline reagent and heating at 120° C. for 10 minutes.

Figure 1:
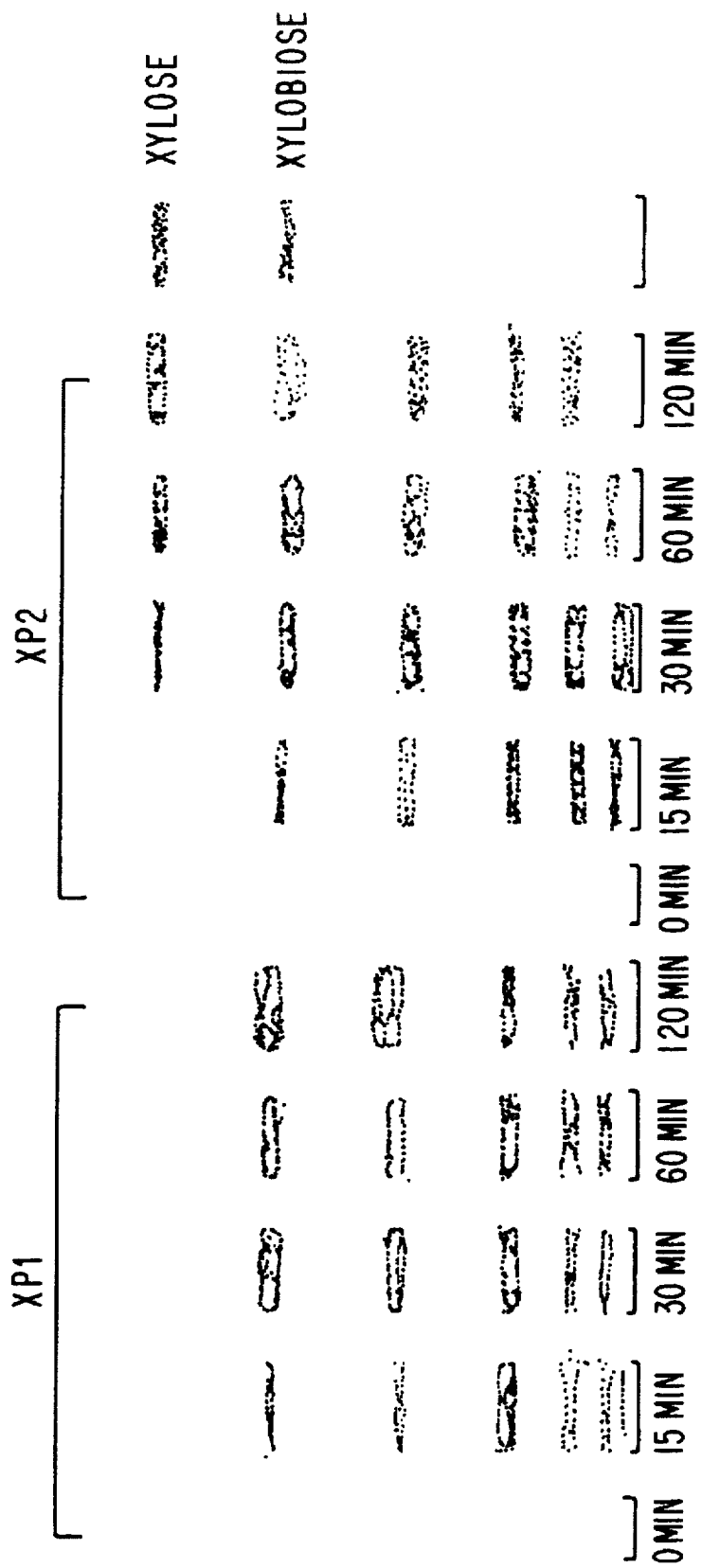
FIG. 1 shows the results of a thin-layer chromatographic analysis of the reaction products generated by treating birch xylan with the enzyme of the present invention.

The results are shown in FIG. 1. The number of minutes shown in this FIG. represents the reaction time of the enzyme.

From these results, it is clear that XP1 produces xylooligosaccharides and XP2 xylose and xylooligosaccharides upon acting on xylan.

ii. Substrate Specificity

XP1 and XP2 act on prepared xylans such as birch xylan and oat spelt xylan, as well as xylan-containing materials such as hardwood kraft pulp and oat spelt bran.

iii. Optimum pH and Stable pH Ranges

For each of the enzymes, the optimum pH and pH stability were determined by using glycine-HCl buffer (pH 3 or below), acetate buffer (pH 4–5), sodium phosphate buffer (pH 6–7), Tris-HCl buffer (pH 8–9) and glycine-NaOH buffer (pH 9.1–10.1). The enzyme activity of each xylanase was measured at each of the pH values.

Figure 2:
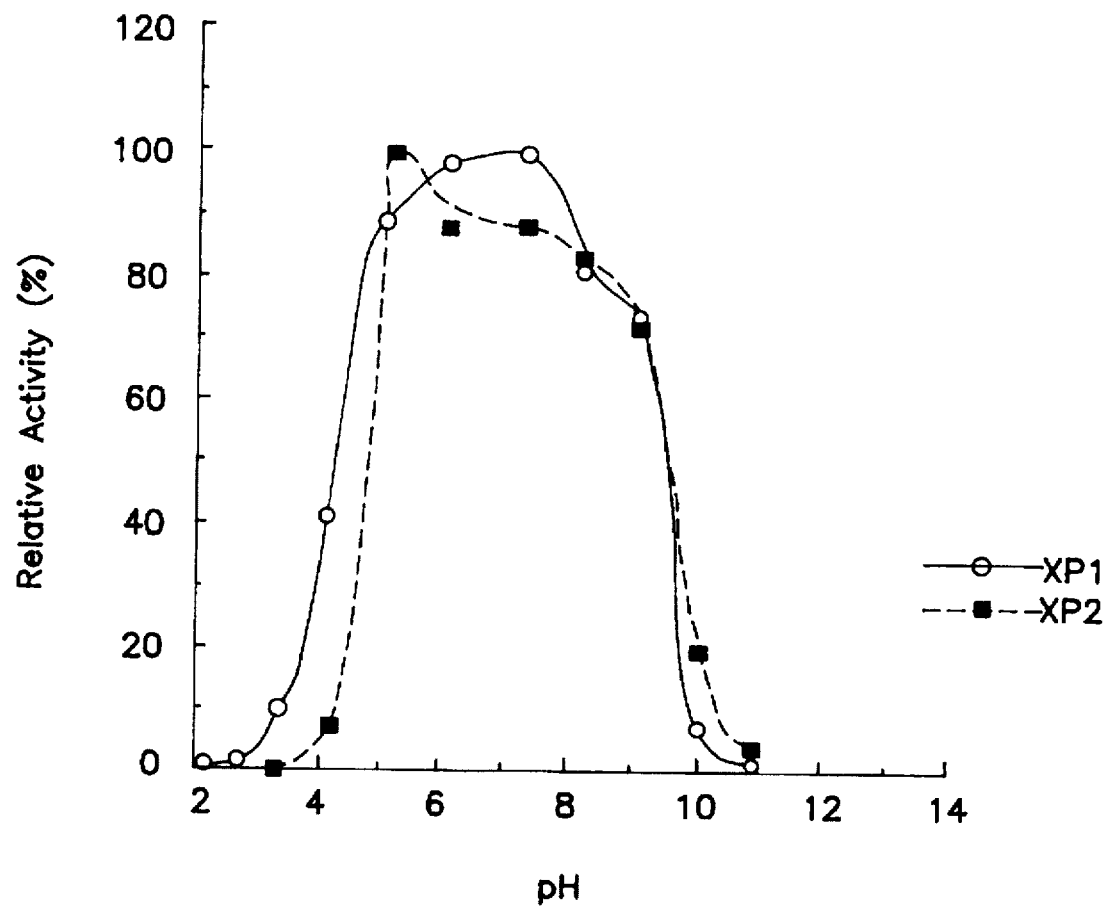
FIG. 2 is a graph showing the optimum pH for reaction of the enzyme of the present invention.

The results are shown in FIG. 2. In this Figure, mark ○ represents XP1 and mark ■ XP2. As seen from this Figure, the optimum pH for enzyme reaction is 5 to 8 for both XP1 and XP2.

In addition, each of the enzymes was retained in a certain 50 mM buffer for two nights and then the enzyme activity was determined.

Figure 3:
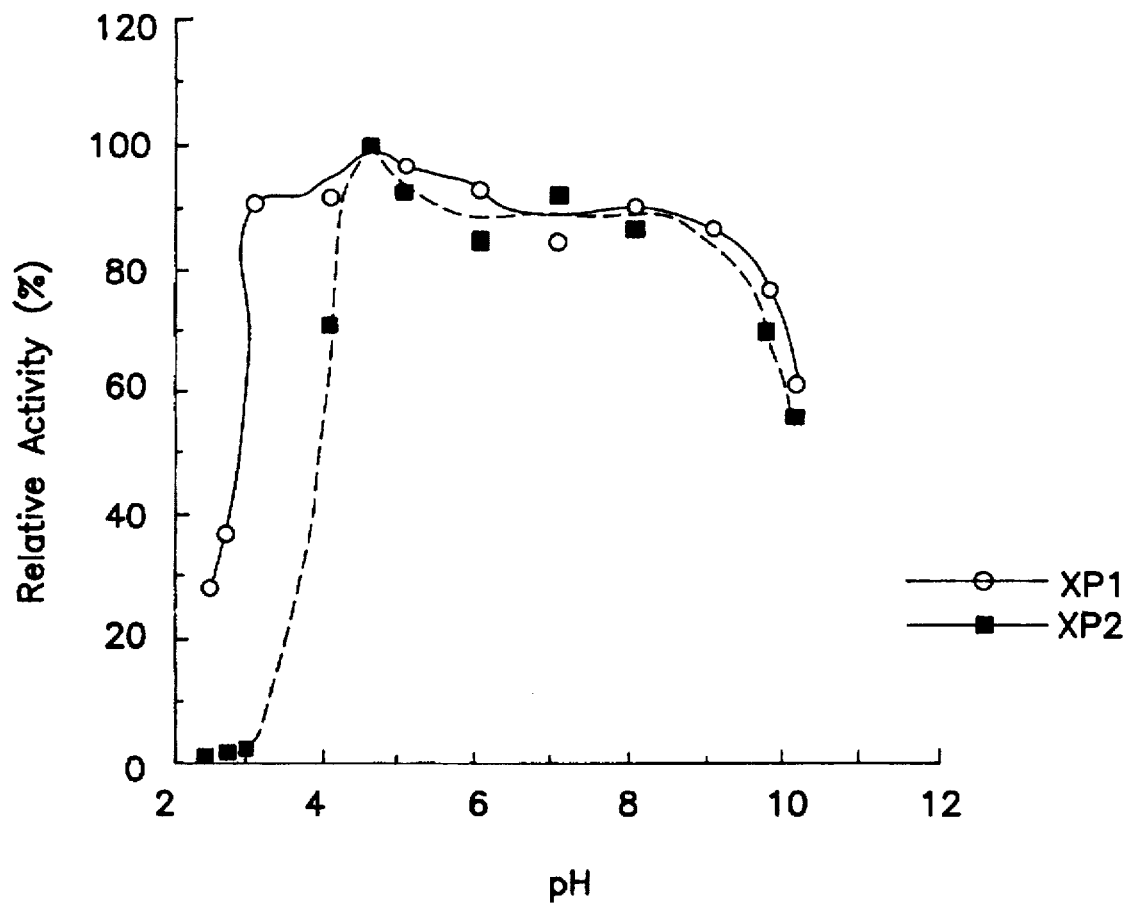
FIG. 3 is a graph showing the pH stability of the enzymes of the present invention.

The results are shown in FIG. 3. In this Figure, mark ○ represents XP1 and mark ■ XP2. As seen from this Figure, XP1 is stable at pH 3.0–9.0 and XP2 at pH 4.5–9.0.

iv. Method for Determination of the Titer

The determination of xylanase activity was carried out as follows.

Fifty microliters of a sample solution is added to 200 μl of 1% birch xylan (Sigma) solution (pH 6.5, in 1/10 McIlvaine buffer), and reacted at 70° C. for 5 minutes. Five hundreds microliters of DNS reagent is added thereto and boiled for 5 minutes. Then, the reaction mixture is immediately ice-cooled and 4 ml distilled water is added thereto. Thereafter, absorbance at 500 nm is measured. Calibration curves are prepared by using a xylose solution of known concentration.

As to the unit of xylanase activity, one unit (U) was defined as the amount of enzyme which releases 1 μl mol of reducing sugar per minute under the above conditions.

v. Appropriate Temperature Range for Action

The enzyme activity of each enzyme was determined at different temperatures.

Figure 4:
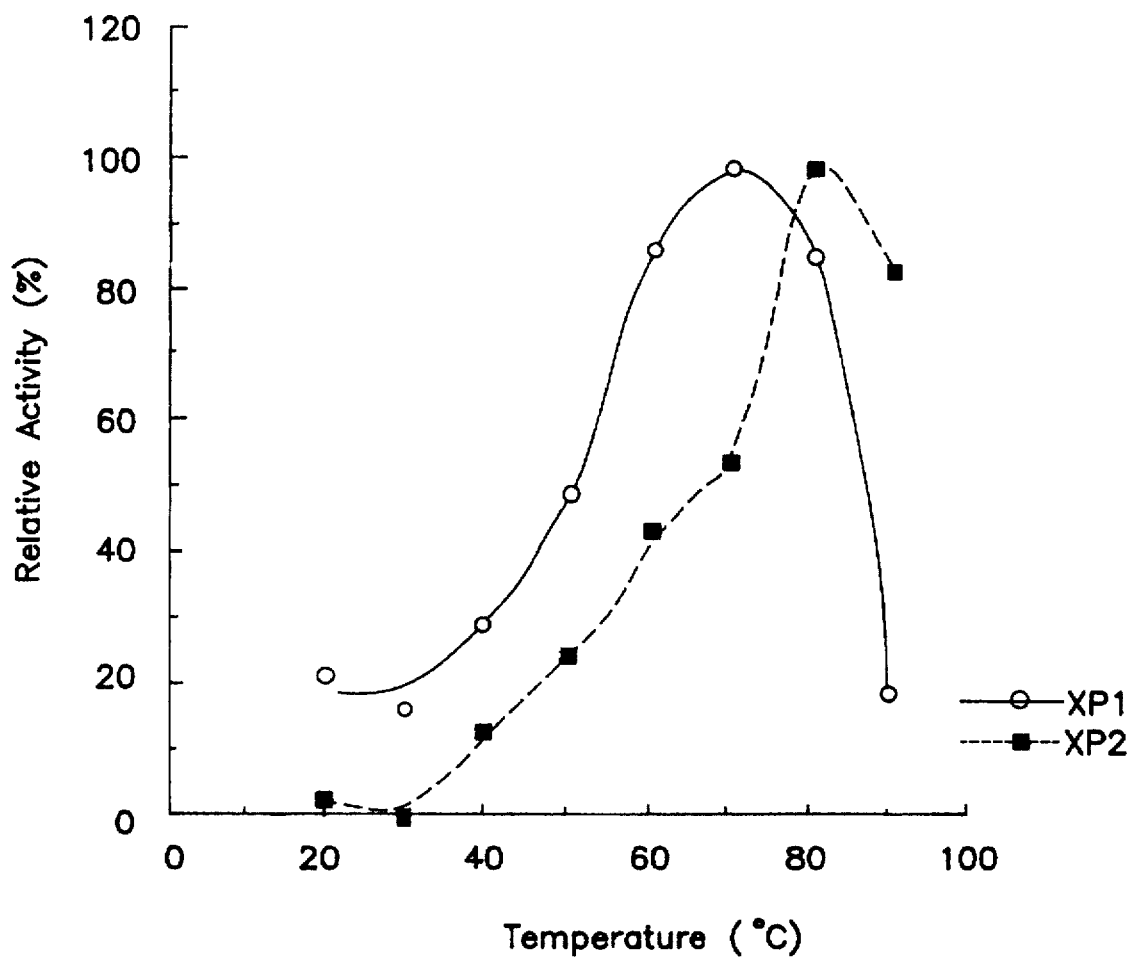
FIG. 4 is a graph showing the optimum temperature for reaction of the enzyme of the present invention.

The results are shown in FIG. 4. In this Figure, mark ○ represents XP1 and mark ■ XP2. As seen from this Figure, the optimum temperature is 70° C. for XP1 and 80° C. for XP2.

In addition, after each enzyme was left in 50 mM Tris-HCl buffer (pH 7.2) for 30 minutes at a certain temperature, the enzyme activity was determined.

Figure 5:
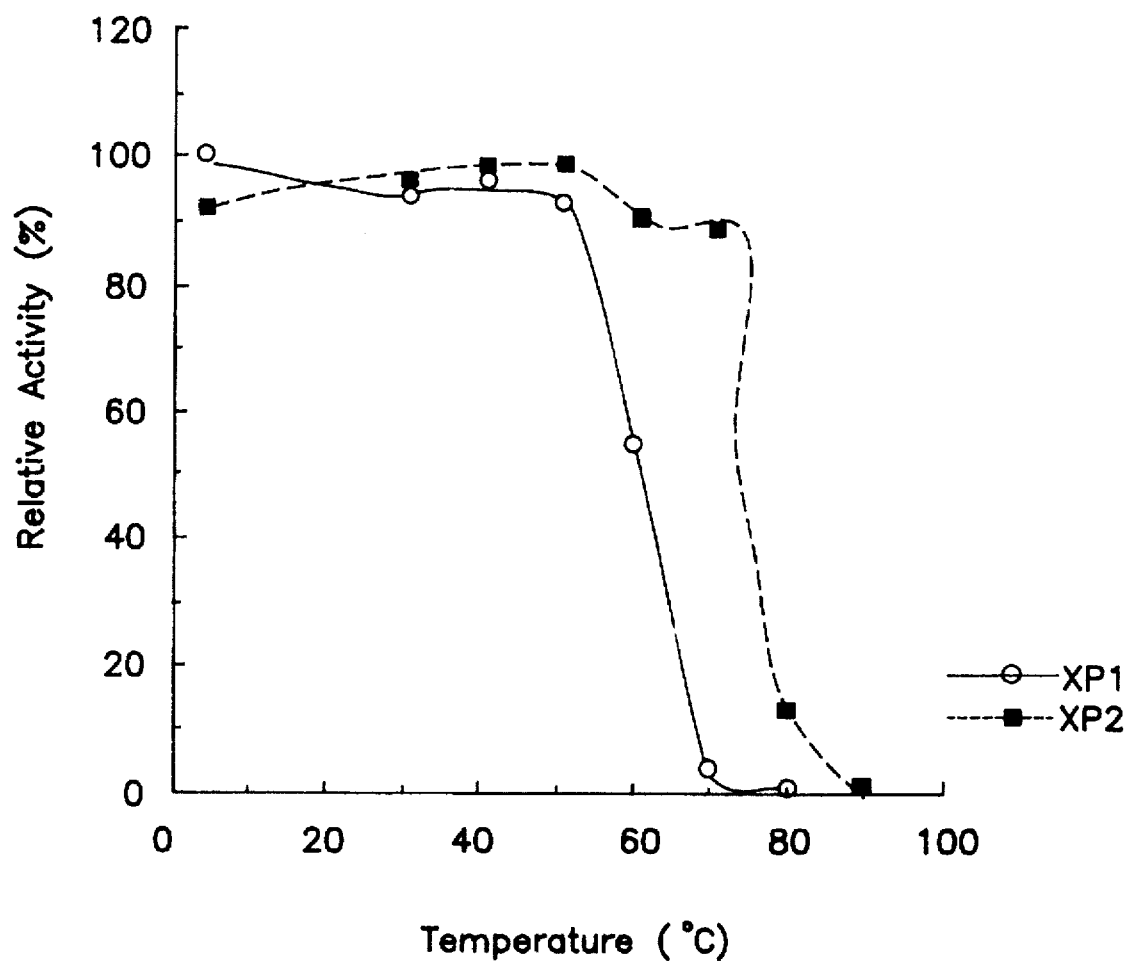
FIG. 5 is a graph showing the thermostability of the enzyme of the present invention.

The results are shown in FIG. 5. In this Figure, mark ○ represents XP1 and mark ■ XP2. As seen from this Figure, XP1 retains about 90% or more of its enzyme activity after a 30 min treatment at 50° C. and exhibits a residual activity of about 50% or more even after a 30 min treatment at 60° C.

On the other hand, XP2 exhibits a residual activity of about 90% or more after a 30 min treatment at 70° C.

vi. Isoelectric Point

As a result of isoelectric focusing using Precoat (Serva, pH 3–10), the isoelectric point of XP1 was found at 8.1 and that of XP2 at 8.5.

vii. Molecular Weight

The molecular weight of XP1 was approximately 22,500 and that of XP2 approximately 32,000 as determined by SDS polyacrylamide gel electrophoresis.

viii. Effects of Metal Ions and Inhibitors

Various metal salts were added to each of the enzyme solutions to a concentration of 1 mM and retained at 4° C. overnight. Then, a metal salt of the same kind was also added to a reaction mixture to a concentration of 1 mM, and the enzyme activities of XP1 and XP2 were determined.

The results are shown in Table 1. As seen from this Table, XP1 is strongly inhibited by $Hg^{2+}$, while XP2 is weakly inhibited by $Mn^{2+}$, $Co^{2+}$ and $Cu^{2+}$ and strongly inhibited by $Hg^{2+}$.

TABLE 1

| Metal Salt | Relative Activity(%) | |
|---|---|---|
| (1 mM) | XP1 | XP2 |
| None | 100 | 100 |
| LiCl | 128 | 99 |
| $MgCl_2$ | 129 | 103 |
| $FeSO_4$ | 165 | 99 |
| $BaCl_2$ | 137 | 108 |
| $AlCl_3$ | 110 | 100 |
| $MnCl_2$ | 99 | 74 |
| $CaCl_2$ | 106 | 98 |
| $CoCl_2$ | 107 | 70 |
| $NiCl_2$ | 129 | 93 |
| $CuCl_2$ | 87 | 68 |
| $HgCl_2$ | 24 | 0 |
| RbCl | 121 | 98 |

Various inhibitors and the like were added to each of the enzyme solutions to a concentration of 1 mM and retained at 4° C. overnight. Then, the same substance was also added to a reaction mixture to a concentration of 1 mM, and the enzyme activities of XP1 and XP2 were determined.

The results are shown in Table 2. As seen from this Table, XP1 is weakly inhibited by iodoacetic acid and EDTA and strongly inhibited by SDS. XP2 is weakly inhibited by EDTA and iodoacetic acid and strongly inhibited by SDS.

TABLE 2

| Inhibitor | Relative Activity(%) | |
|---|---|---|
| (1 mM) | XP1 | XP2 |
| None | 100 | 100 |
| SDS | 0 | 0 |
| EDTA | 59 | 65 |
| $NaN_3$ | 96 | 109 |
| Iodoacetic acid | 75 | 76 |
| Dithiothreitol | 85 | 82 |

The enzymes of the invention are thermostable xylanases of which the optimum temperature for reaction is 70° C. or above. They are novel thermostable xylanases having physicochemical properties which are different from those of conventional thermostable xylanases. With respect to conventional thermostable xylanases, the following papers have been reported.

John et al. reported xylanase IA derived from *Aspergillus niger* Strain 21 having an optimum pH for reaction of 5.5–6 and an optimum temperature for reaction of 65°–80° C. (Can. J. Biochem., 57, 125, 1979). However, the isoelectric point of this enzyme is not described and its molecular weight is 50,000.

Berenger et al. isolated three *Clostridium stercorarium*-derived xylanases (A, B and C) having an optimum pH for reaction of 6–7 and an optimum temperature for reaction of 75° C. (Can. J. Microbiol., 31, 635, 1985). However, all of these three enzymes have an isoelectric point of about 4.5 and their molecular weights range from 44,000 to 72,000.

Wang et al. isolated *Streptomyces cyaneus*-derived xylanase I having an optimum pH for reaction of 8.5 and an optimum temperature for reaction of 72° C. (J. Gen. Microbiol. 139, 1987, 1993). However, the molecular weight of this enzyme is 37,000 and its isoelectric point is 5.1.

With respect to Bacillus-derived xylanases, Honda et al. isolated from Bacillus C-125 strain xylanase N having an optimum pH for reaction of 6–7 and an optimum temperature for reaction of 70° C. as well as xylanase A having an optimum pH for reaction of 6–10 and an optimum temperature for reaction of 70° C. (Can. J. Microbiol., 31, 538, 1985). However, the molecular weights of these enzymes are 16,000 and 43,000.

A Bacillus-derived xylanase is disclosed in Japanese Unexamined Patent Publication/PCT No. 6–506107 which has an optimum pH for reaction of 4.8–7.0 and is stable at 60° C. However, the molecular weight of this enzyme is 22,000 and its isoelectric point is 7.7. There is no description about the optimum temperature for reaction of this enzyme.

Since these known xylanases are different from the xylanases of the present invention in optimum temperature, optimum pH, molecular weight, isoelectric point and the like as so far described, XP1 and XP2 of the present invention have been recognized as novel thermostable xylanases.

The results of comparison between the enzymes of the present invention and conventional xylanases are shown in Table 3.

TABLE 3

| Strain | Optimum Temperature (°C.) | Optimum pH | Isoelectric point | Molecular weight | Reference |
|---|---|---|---|---|---|
| 2113 | 70 | 5–8 | 8.1 | 22500 | Present invention (XP1) |
|  | 80 | 5–8 | 8.5 | 32000 | Present invention (XP2) |
| W1 | 65 | 6.0 | 8.5 | 21500 | Agric. Biol. Chem., 49, |
| W2 | 65 | 6.0 | 8.3 | 22500 | 2033, 1985 |
| 21 | 60 | 7.0 | 5.1 | 39500 | J. Bac. 172, 12, 6669, 1990 |
| 11-1s | 80 | 4.0 | — | 56000 | Agric. Biol. Chem., 45, 1121, 1981 |
| C-125 | 70 | 6–7 |  | 16000 | Can. J. Microbiol., 31, |
|  | 70 | 7–10 |  | 43000 | 538, 1985 |
| 21 (3 enzymes) | 75 | 6–7 | 4.5 | 44000–72000 | Can. J. Biochem., 57, 125, 1979 |
| Clostridium | 72 | 8.5 | 5.1 | 37500 | Can. J. Microbiol., 31, 635, 1985 |
| Streptomyces | 70 | 6–7 | — | 16000 | J. Gen. Microbiol., 13, 1987, 1993 |
| I-1017 | — Stable at 60° C. | 4.8–7 | 7.7 | 22000 | Japanese Unexamined Patent Publication/PCT No. 6-506107 |

(2) Microorganisms

Microorganisms which produce the thermostable xylanase of the present invention will be described below.

The microorganism used in the present invention is a strain belonging to the genus Bacillus and having an ability to produce the thermostable xylanase. Specific examples of such microorganism include Bacillus sp. 2113 and Bacillus sp. 208.

Now, each of these microorganisms will be described.

A. Bacillus sp. 2113

Bacillus sp. 2113 is a strain which the present inventors have isolated from a soil. (Accession No. FERM BP-5264, deposited on Nov. 14, 1994 with the National Institute of Bioscience and Human-Technology Agency of Industrial Science and Technology, Japan, under the terms of the Budapest Treaty) This strain grows well when cultured at 45° C. on a medium containing 1% birch xylan or oat spelt xylan, 0.5% peptone, 0.5% yeast extract, 0.1%, $K_2HPO_4$ and 0.02% $MgSO_4 \cdot 7H_2O$ (pH 7. 0). Bacteriological characteristics of this strain are as follows.

i) Morphological Properties

1) The cells are motile rods, 0.3–0.6 by 2–5 μm in size, occuring often in chains of 2–3 cells. The endospores are formed and spindle.

2) The cells are Gram-variable and not acid-fast.

ii) The Growth on Various Media (The temperature for growth was 45° C.)

1) Colonies on nutrient agar (1% Difco beef extract, 1% bacto peptone, 0.5% NaCl, 1, 1.5% agar, pH 7.0), are almost circular and slightly undulate. These colonies are slightly glossy and translucent. Colonies on nutrient slant (1% Difco beef extract, 1% bacto peptone, 0.5% NaCl , 1.5% agar, pH 7.0) are slightly glossy and spreading. Growth in nutrient broth media (1% Difco beef extract, 1% bacto peptone, 0.5% NaCl, 1.5% agar, pH 7.0) are weak and cells sediment to the bottom. Growth on any of the above media is weak. The growth is worse on nutrient agar (0.8% Difco nutrient broth, 1.5% agar, pH 7.0).

2) The microorganism grows on nutrient agar (1% Difco beef extract, 1% bacto peptone,0.5% NaCl, 1.5% agar, pH 7.0) containing 2% NaCl. However, it does not grow on the medium containing 5% NaCl.

3) On nutrient broth with gelatin (1% Difco beef extract, 1% peptone, 0.5% NaCl, 12% gelatin, pH 7.0), the microorganism does not liquefy gelatin.

iii) Physiological characteristics of this microorganism are shown in Table 4.

TABLE 4

| (1) Reduction of nitrates | − |  |
|---|---|---|
| (2) VP | − |  |
| (3) Production of indole | − |  |
| (4) Hydrolysis of casein | − |  |
| (5) Hydrolysis of gelatin | − |  |
| (6) Hydrolysis of starch | + |  |
| (7) Utilization of citric acid | − | (Simmons) |
|  | − | (Koser) |
|  | ± | (Christensen) |
| (8) Urease | + |  |
| (9) Oxidase | + |  |
| (10) Catalase | + |  |
| (11) Production of gas from glucose | − |  |
| (12) Production of acid from sugars |  |  |
| xylose + mannit + | | |
| fructose + arabinose + | | |
| glycerol + saccharose + | | |
| glucose + raffinose + | | |
| mannose + maltose + | | |
| lactose + trehalose + | | |
| sorbit + rhamnose + | | |
| galactose + | | |
| (13) Temperature range for growth | 20–55° C. |  |
| Optimum temperature for growth | 35–50° C. |  |
| (14) pH range for growth | 5–9 |  |
| Optimum pH range for growth | 6–8 |  |
| (15) Does not produce cellulase. | | |

Based on the bacteriological characteristics described above, the inventors have identified the subject strain according to Bergey's Manual of Systematic Bacteriology.

As a result, it is clear that this strain belongs to the genus Bacillus because it is a spore-forming rods being Gram-variable and yet catalase positive. With respect to species, this strain is close to Bacillus circulans. However, while the strain of the present invention is oxidase positive and able to grow even at 55° C., Bacillus circulans is oxidase negative and unable to grow at 50° C. or above. Therefore, the strain of the invention is not identical with Bacillus circulans.

When compared with *Bacillus stearothermophilus* which has been reported to produce a thermostable xylanase (T. Nanmori et al., J. Bacteriol., 172:6669, 1990), the strain of the present invention has spindle spores, cannot hydrolyze gelatin and cannot grow at 65° C., whereas *Bacillus stearothermophilus* has spores terminally, can hydrolyze gelatin and can grow at 65° C. Accordingly, the strain of the invention is not identical with *Bacillus stearothermophilus*.

Xylanase-producing Bacillus No. I-1017 and No. I-1018 described in Japanese Unexamined Patent Publication/PCT No. 6-506107 have an optimum temperature for growth at 62° C. and do not utilize fructose nor arabinose. By contrast, the strain of the invention has an optimum temperature for growth at 35°–50° C. and utilize fructose and arabinose. Accordingly, the strain of the invention is not identical with Bacillus No. I-1017 nor No. I-1018.

As so far described, there is no species with which the strain of the invention can be identified. Therefore, the strain of the invention has been judged a novel strain and designated as *Bacillus sp.* 2113. *Bacillus sp.* 2113 has been deposited at the National institute of Bioscience and Human-technology, Agency of Industrial Science and Technology, Ministry of International Trade and Industry under the Accession No. of FERM BP-5264.

B. *Bacillus sp.* 208

*Bacillus sp.* 208 grows well at 45° C. on a medium containing 1% birch xylan or oat spelt xylan, 0.5% peptone, 0.5% yeast extract, 0.1% $K_2HPO_4$ and 0.02% $MgSO_4 \cdot 7H_2O$ (pH 7.0). Bacteriological characteristics of this strain are as follows.

i) Morphological Properties

1) The cells are motile rods, 0.3–0.6 by 2–5 μm in size, occuring often in chains of 2–3 cells. The endospores are formed and spindle.

2) The cells are gram-variable and not acid-fast.

ii) Growth on Various Media (The temperature for growth was 45° C.)

1) Colonies on nutrient agar (0.8% Difco nutrient broth, 1. 5% agar, pH 7.0), are almost circular and slightly undulate. These colonies are slightly glossy and translucent and grow well.

2) The microorganism grows on nutrient agar (0.8% Difco nutrient broth, 1.5% agar, pH 7) containing 2% NaCl. However, it does not grow on the medium containing 5% NACl.

3) On nutrient broth with gelatin (1% Difco beef extract, 12% gelatin, pH 7.0), the microorganism does not liquefy gelatin.

iii) Physiological characteristics of this microorganism are shown in Table 5.

TABLE 5

| (1) Reduction of nitrates | − | |
|---|---|---|
| (2) VP | − | |
| (3) Production of indole | − | |
| (4) Hydrolysis of gelatin | − | |
| (5) Hydrolysis of casein | − | |
| (6) Hydrolysis of starch | + | |
| (7) Utilization of citric acid | − | (Simmons) |
| | − | (Koser) |
| | − | (Christensen) |
| (8) Urease | + | |
| (9) Oxidase | + | |
| (10) Catalase | + | |
| (11) Production of gas from glucose | − | |

TABLE 5-continued

| (12) Production of acid from sugars | | | |
|---|---|---|---|
| xylose | + | lactose | + |
| glucose | + | sorbitol | + |
| galactose | + | mannose | + |
| maltose | + | mannitol | + |
| arabinose | + | | |
| (13) Temperature range for growth | | 20–55° C. | |
| Optimum temperature for growth | | 35–50° C. | |
| (14) pH range for growth | | 5–9 | |
| Optimum pH range for growth | | 6–8 | |
| (15) Does not produce cellulase. | | | |

Based on the bacteriological characteristics described above, the inventors have identified the subject strain according to Bergey's Manual of Systematic Bacteriology.

As a result, it is clear that this strain belongs to the genus Bacillus because it is a spore-forming rods being aerobic, indefinite in Gram-variable and yet catalase positive.

With respect to species, the characteristics of this strain resemble those of *Bacillus circulans*. However, while the temperature range for growth of *Bacillus circulans* is 10°–40° C. and it is oxidase negative, the strain of the present invention (*Bacillus sp.* 208) is able to grow at high temperature (40°–60° C.) under which *Bacillus circulans* cannot grow, and is oxidase positive. Therefore, the strain of the invention is not identical with *Bacillus circulans*.

When compared with *Bacillus stearothermophilus* which has been reported to produce a thermostable xylanase (T. Nanmori et al., J. Bacteriol., 172:6669, 1990), the strain of the present invention has spindle spores and cannot hydrolyze gelatin, whereas *Bacillus stearothermophilus* has spores terminally and can hydrolyze gelatin. Accordingly, the strain of the invention is not identical with *Bacillus stearothermophilus*.

While xylanase-producing Bacillus No. I-1017 and No. I-1018 described in Japanese Unexamined Patent Publication/PCT No. 6-506107 do not utilize arabinose, the strain of the invention utilize arabinose. Accordingly, the strain of the invention is not identical with Bacillus No. I-1017 nor No. I-1018.

Thus, the subject strain of the invention resembles *Bacillus sp.* 2113 mentioned above. However, while *Bacillus sp.* 2113 does not grow well on nutrient agar (0.8% Difco nutrient broth and 1.5% agar), the subject strain grows well on this nutrient agar. Therefore, it is believed that the subject strain can be distinguished from *Bacillus sp.* 2113. The subject strain has been judged a novel strain and designated as *Bacillus sp.* 208.

*Bacillus sp.* 208 has been deposited at the National institute of Bioscience and Human-technology, Agency of Industrial Science and Technology, Ministry of International Trade and Industry under the Accession No. of FERM BP-5321.

(3) Cloning of a Thermostable Xylanase Gene

A DNA library is prepared to clone a xylanase gene

This DNA library may be prepared by extracting a chromosomal DNA from *Bacillus sp.* 2113 or *Bacillus sp.* 208, treating the chromosomal DNA with appropriate restriction enzymes, ligating a resultant fragment to an appropriate vector and then introducing this vector into an appropriate host.

Conventional methods may be used to extract a chromosomal DNA from *Bacillus sp.* 2113 or *Bacillus sp.* 208 (e.g., the method of Blin and Stafford in Molecular Cloning, Cold Spring Harbor Laboratory (1982)). Then, the chromosomal DNA obtained is treated with appropriate restriction enzymes for partial digestion and subsequently subjected to sucrose density-gradient centrifugation to thereby obtain fractions of 3–5 kbp fragments. The thus obtained DNA fragment is inserted into a cloning vector which has been treated with specific restriction enzymes that generate the same cohesive ends as those of the fragment. Examples of the vector used in the preparation of a DNA library include plasmid vectors and phage vectors. Examples of the host include E. coli and yeast.

As a cloning vector, for example, pUC cloning vectors may be used. For the isolation of a gene of interest from the DNA library obtained, E. coli is transformed by using the DNA library and spread on a xylan medium, and then the formation of a halo is observed as an indicator.

The nucleotide sequence of the cloned DNA may be analyzed by the dideoxy chain termination method, Maxam-Gilbert method and the like using a radioactive or fluorescent label.

(4) Method of Production of the Enzyme

Hereinbelow, the method for producing the enzyme of the invention will be described.

i. Purification of the Enzyme of the Invention from a Culture of the Thermostable Xylanase-Producing Microorganism A thermostable xylanase may be produced by culturing *Bacillus sp.* 2113 or sp. 208 of the invention. As carbon and nitrogen sources for cultivation, any substance may be used as long as it can be utilize to produce a thermostable xylanase. Examples of carbon sources include xylan and xylan-containing oat spelt bran, wheat bran, pulp, bagasse, corn fiber, agricultural wastes such as rice straw and plant fiber. Examples of nitrogen sources include yeast extract, peptone, various amino acids, soy bean, corn steep liquor and nitrogen compounds such as various inorganic nitrogen compounds. Further, various salts, vitamins, minerals and the like may be used appropriately.

The cultivation temperature and pH are not particularly limited as long as they allow the microorganism to grow and produce a thermostable xylanase. The cultivation temperature is from 20° to 55° C., preferably from 35° to 50° C., and the pH is from 5 to 9, preferably from 6 to 8.

After the cultivation of the microorganism of the invention and the separation of cells, a culture filtrate may be used as a crude enzyme solution of a thermostable xylanase. Such a crude enzyme solution of a thermostable xylanase has an optimum temperature for reaction ranging from 60° to 80° C. and an optimum pH ranging from 5 to 7.

A thermostable xylanase may be concentrated or caked by dialysis, salting out, ultrafiltration, lyophilization and the like. Further, thermostable xylanases XP1 and XP2 may be purified from culture filtrate by appropriately combining or repeating methods such as molecular weight fractionations by gelfiltration, ammonium sulfate fractionation, various ion exchange resins, hydroxyapatite, isoelectric point fractionation and the like. Specific purification methods are described in Examples infra.

ii. Purification of a Recombinant Thermostable Xylanase with Recombinant Techniques The thermostable xylanase of the invention may also be purified by expressing a cloned gene. (In the present invention, a thermostable xylanase obtained by gene expression is referred to as "a recombinant thermostable xylanase".) Specifically, the enzyme of the invention may be produced at a high yield by expressing the gene obtained in (3) above using an appropriate host/vector system. A plasmid vector, a phage vector or the like is mainly used as a vector for this expression. *E. coli, Bacillus subtilis*, yeast or the like is mainly used as a host. As carbon and nitrogen sources for culturing, any substance may be used as long as it can be utilize to produce a thermostable xylanase. Examples of carbon sources include xylan and xylan-containing oat spelts bran, wheat bran, pulp, bagasse, corn fiber, agricultural wastes such as rice straw and plant fiber. Examples of nitrogen sources include yeast extract, peptone, various amino acids, soybean, corn steep liquor and nitrogen compounds such as various inorganic nitrogen compounds. Further, various salts, vitamins, minerals and the like may be used appropriately. The cultivation temperature and pH are not particularly limited as long as they allow the microorganism to grow and produce a thermostable xylanase. The cultivation temperature is preferably 37° C., and the pH is preferably 7. As methods for purifying the enzyme, it may be purified by appropriately combining or repeating the methods such as molecular weight fractionations by gel filtration, ammonium sulfate fractionation, various ion exchange resins, hydroxyapatite, isoelectric point fractionation and the like. It is possible to recognize whether the purified enzyme is same as the enzyme produced by *Bacillus sp.* 2113 by comparing the molecular weight, optimum pH, optimum temperature, N-terminal amino acid sequence and the like. Specific methods for obtaining the recombinant xylanase are described in Examples (infra).

(5) Method for Bleaching Pulp

A method for bleaching pulp by using the enzyme of the invention will be described. In the process of manufacturing chemical pulp or mechanical pulp, the pulp may be bleached by treating thermostable xylanase XP1 (including recombinant XP1) and/or XP2 (including recombinant XP2) of the invention and/or a culture of *Bacillus sp.* 2113 or *Bacillus sp.* 208 belonging to the genus Bacillus. Furthermore, the pulp may be bleached by chemicals and/or an alkali extraction before, after or during the above-mentioned enzyme treatment.

The amount of the above-mentioned culture or enzyme for treating pulp was 0.1–5 u/g, preferably 0.5–3 u/g of pulp (bone dry weight). Reaction conditions are as follows. When a culture filtrate (crude enzyme solution) is used, the reaction temperature is 50°–90° C. and the pH is 5–8. When a purified enzyme is used, the reaction temperature and pH for XP1 are 50°–80° C. and 5–8, respectively, and those for XP2 are 60°–90° C. and 5–8, respectively. The reaction time is 0.2–24 hours, preferably 0.5–8 hours. Chlorine, chlorine dioxide, nitrogen dioxide, hypochlorites, hydrogen, oxygen peroxide, ozone and the like may be used for bleaching chemicals. For alkali extraction, a number of alkaline chemicals well known in pulp and paper industry may be used. An alkali extraction may be carried out with 0.5 to 3% (converted into NaOH) /g of pulp (bone dry weight), and also, an alkali extraction may be crried out in company with the addition of oxygen, hydrogen peroxide and the like.

PREFERRED EMBODIMENTS OF THE INVENTION

Now, the present invention will be described more specifically below with reference to the following Examples, which should not be construed as limiting the scope of the invention.

EXAMPLE 1

Preparation of a Crude Enzyme Solution (1)

A test tube (25 mm in inner diameter) with paper plug containing 10 ml liquid medium was autoclaved at 121° C.

for 15 min. The medium contained 0.6% birch xylan (Sigma), 0.5% peptone, 0.5% yeast extract, 0.1% $K_2HPO_4$ and 0.02% $MgSO_4 \cdot 7H_2O$ (pH 7.0). In this medium, one loop-ful of *Bacillus sp.* 2113 was inoculated and cultivated on reciprocal shaker (amplitude: 25 mm, 300 reciprocations/min) at 45° C. After the cultivation, the culture was centrifuged (at 10,000 rpm for 10 min) to separate the supernatant. Thus, a crude enzyme solution containing thermostable xylanase was obtained.

Fifty microliters of the crude enzyme solution was added to 200 μl of 1% birch xylan (Sigma) solution (in 1/10 McIlvaine buffer, pH 6. 5), and reacted at 70° C. for 5 minutes.

After addition of DNS reagent (500 μl) and subsequent boiling for 5 minutes, the reaction mixture was immediately ice-cooled and 4 ml of distilled water was added thereto. Then, absorbance at 500 nm was measured. Calibration curves were prepared by using a xylose solution of known concentration.

As to the unit of xylanase activity, one unit (U) was defined as the amount of enzyme which releases 1 μmol of reducing sugar per minute under the above conditions.

As a result, the thermostable xylanase activity in the culture supernatant was 400 U/ml for 24 hours and 500 U/ml for 48 hours.

EXAMPLE 2

Preparation of a Crude Enzyme Solution (2)

A test tube (25 mm in inner diameter) with paper plug containing 10 ml liquid medium was autoclaved at 121° C. for 15 minutes. The medium contained 0.6% birch xylan (Sigma), 0.5% peptone, 0.5% yeast extract, 0.1% $K_2HPO_4$ and 0.02% $MgSO_4 \cdot 7H_2O$ (pH 7.0). In this medium, one loop-ful of *Bacillus sp.* 208 was inoculated and cultivated on reciprocal shaker (amplitude: 25 mm, 300 reciprocations/min). After the cultivation, the culture was centrifuged (at 10,000 rpm for 10 min) to separate the supernatant. Thus, a crude enzyme solution containing thermostable xylanase was obtained. The thermostable xylanase activity in the culture supernatant was assayed by the following methods.

Fifty microliters of the crude enzyme solution was added to 200 μl of 1% birch xylan (Sigma) solution (in 1/10 McIlvaine buffer, pH 6.3), and reacted at 70° C. for 5 minutes.

After addition of DNS reagent (500 μl) and subsequent boiling for 5 minutes, the reaction mixture was immediately ice-cooled and 4 ml of distilled water was added thereto. Then, absorbance at 500 nm was measured. Calibration curves were prepared by using a xylose solution of known concentration.

As to the unit of xylanase activity, one unit (U) was defined as the amount of enzyme which releases 1 μmol of reducing sugar per minute under the above conditions.

As a result, the thermostable xylanase activity in the culture supernatant was 400 U/ml for 24 hours and 500 U/ml for 48 hours.

EXAMPLE 3

Purification of the Thermostable Xylanase

A 500 ml conical flask with cotton plug containing 50 ml liquid medium was autoclaved at 121° C. for 15 min. The medium contained 0.6% birch xylan (Sigma), 0.5% peptone, 0.5% yeast extract, 0.1% $K_2HPO_4$ and 0.02% $MgSO_4 \cdot 7H_2$ (pH 7.0). One milliliter of the culture obtained in Example 1 was inoculated and incubated at 45° C. for 3 days on reciprocal shaker (amplitude: 10 cm, 100 reciprocations/min). After the incubation, the culture was centrifuged (at 8,000 rpm for 10 min). To the supernatant ammonium sulfate was added to 20–60% saturation. The resulting precipitate was collected by centrifugation (at 20,000 rpm for 10 min), and then dialyzed against 20 mM Tris-HCl buffer (pH 7.2). The enzyme solution was charged onto ion CM Toyopearl 650-C column (2.5 cm dia.×30 cm) equilibrated with 20 mM acetate buffer (pH 5.0).

The adsorbed fractions were eluted with a linear gradient of from 0 to 0.3M Nacl in the acetate buffer and fractionated by 5.3 ml.

As a result, xylanase activity was separated into two peaks; the active fraction eluted earlier was designated as xylanase XP1 and the active fraction eluted later as xylanase XP2.

Active fractions of each xylanase were pooled and subjected to ammonium sulfate fractionation again. To each fraction, ammonium sulfate was added to 20–60% saturation and the resulting precipitate was collected by centrifugation (at 20,000 rpm for 10 min) and then charged onto Sephacryl S-200 column (2.5 cm dia.×93 cm) equilibrated with 20 mM Tris-HCl buffer (pH 7.2) containing 50 mM NaCl. The adsorbed fractions were eluted with the Tris-HCl buffer. For XP1, flow rate was 34 ml/hr and the eluate was fractionated by 5 ml. For XP2, flow rate was 34 ml/hr and the eluate was fractionated by 6.7 ml.

Active fractions of each of these xylanases were pooled and subjected to SDS polyacrylamide gel electrophoresis. As a result, the purification was confirmed to be homogeneous. The yield of each purified enzyme from culture filtrate is 47.8% for XP1 and 7.8% for XP2. The specific activity was 1420 U/mg for XP1 and 919 U/mg for XP2.

EXAMPLE 4

Cloning of the Thermostable Xylanase Gene (1) Preparation of a Chromosomal DNA Library A 500 ml conical flask with cotton plug containing 50 ml liquid medium was autoclaved at 121° C. for 15 min. The medium contained 0.6% birch xylan (Sigma), 0.5% peptone, 0.5% yeast extract, 0.1% $K_2HPO_4$ and 0.02% $MgSO_4 \cdot 7H_2O$ (pH 7.0). In this medium, one loop-ful of *Bacillus sp.* 2113 was inoculated and cultivated on reciprocal shaker (amplitude: 10 cm, 100 reciprocations/min). After the cultivation, the culture was centrifuged (at 10,000 rpm for 10 min) to harvest cells.

The cells were suspended in 5 ml of glucose-lysozyme solution [50 mM glucose, 10 mM EDTA, 25 mM Tris-HCl buffer (pH 8.0), 4 mg/ml lysozyme] and store at room temperature for 15 minutes. Five milliliters of alkali solution (0.2N NaOH, 1% SDS) was added to the suspension and mixed gently. Then, the mixture was cooled on ice for 15 minutes. Thereafter, the mixture was subjected to phenol extraction and chloroform extraction. Ethanol was gradually added to the aqueous layer extracted. When DNA began to deposit, chromosomal DNA was wound round a glass stick and suspended in TE solution. One hundred micrograms of the chromosomal DNA obtained was partially digested with restriction enzyme EcoRI and fractionated by 3–20% sucrose density-gradient ultracentrifugation (at 22,500 rpm for 16 hr). The fractions of 3–5 kbp fragments were recovered by ethanol precipitation.

(2) Transformation of the Thermostable Xylanase Gene into *E. coli*

One microgram of *E. coli* cloning vector pUC19 (Takara Shuzo Co., Ltd.) was completely digested with restriction enzyme EcoRI, dephosphorylated with alkaline phosphatase (derived from calf intestine) and reacted at 16° C. for 16 hours in a ligation buffer containing 500 ng of the DNA obtained by the ethanol precipitation mentioned in (1) above and 2.5 U of T4 DNA ligase, to thereby ligate the gene of the invention to the cloning vector.

By using the DNA library obtained in (1) above, *E. coli* JM109 strain was transformed by the calcium chloride method.

(3) Isolation of the Xylanase Gene from the DNA Library Cloning of the XP1 Gene

The selection of a clone containing the xylanase XP1 gene from the above-mentioned DNA library was carried out by transforming *E. coli* using the DNA library, spreading the cells on a xylan medium and observing the formation of a halo around the colonies as an indicator. Specifically, after the transformation of *E. coli* using the DNA library, the cells were spread on a xylan medium [1% oat spelt xylan (Sigma), 1% peptone, 0.5% yeast extract, 0.5% NaCl, 2% agar, pH 7.0] containing 100 µg/ml of ampicillin and incubated at 37° C. overnight. Then, the formation of a halo was observed. Plasmid DNA was prepared by alkali extraction in large quantity from the clone thus obtained and purified by ultracentrifugation (for 16 hours at 20° C.). Then, the nucleotide sequence of the DNA was determined with a Sequenase Kit (manufactured by United States Biochemical).

The results are shown in SEQ ID NO:2.

The amino acid sequence of xylanase XP1 which is deduced from the above-mentioned nucleotide sequence of the xylanase XP1 gene is shown in SEQ ID NO:1.

Figure 6:
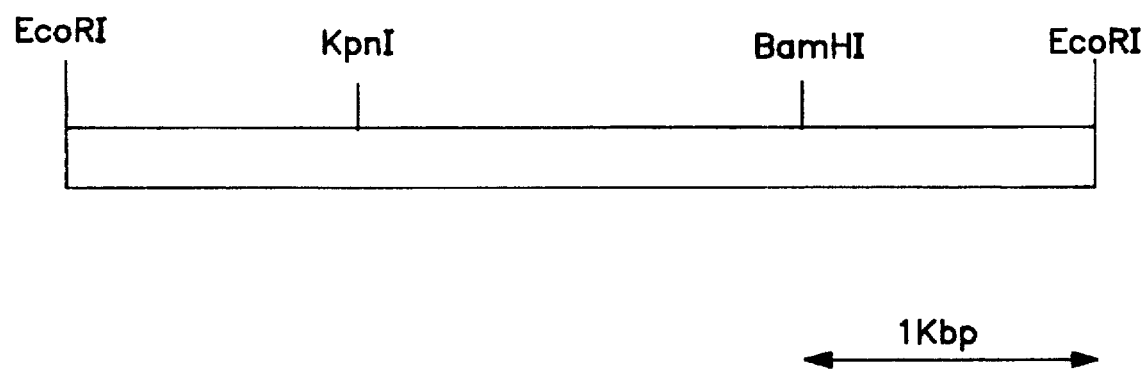
FIG. 6 is the restriction map of a DNA fragment containing the gene coding for xylanase XP1.
Figure 7:
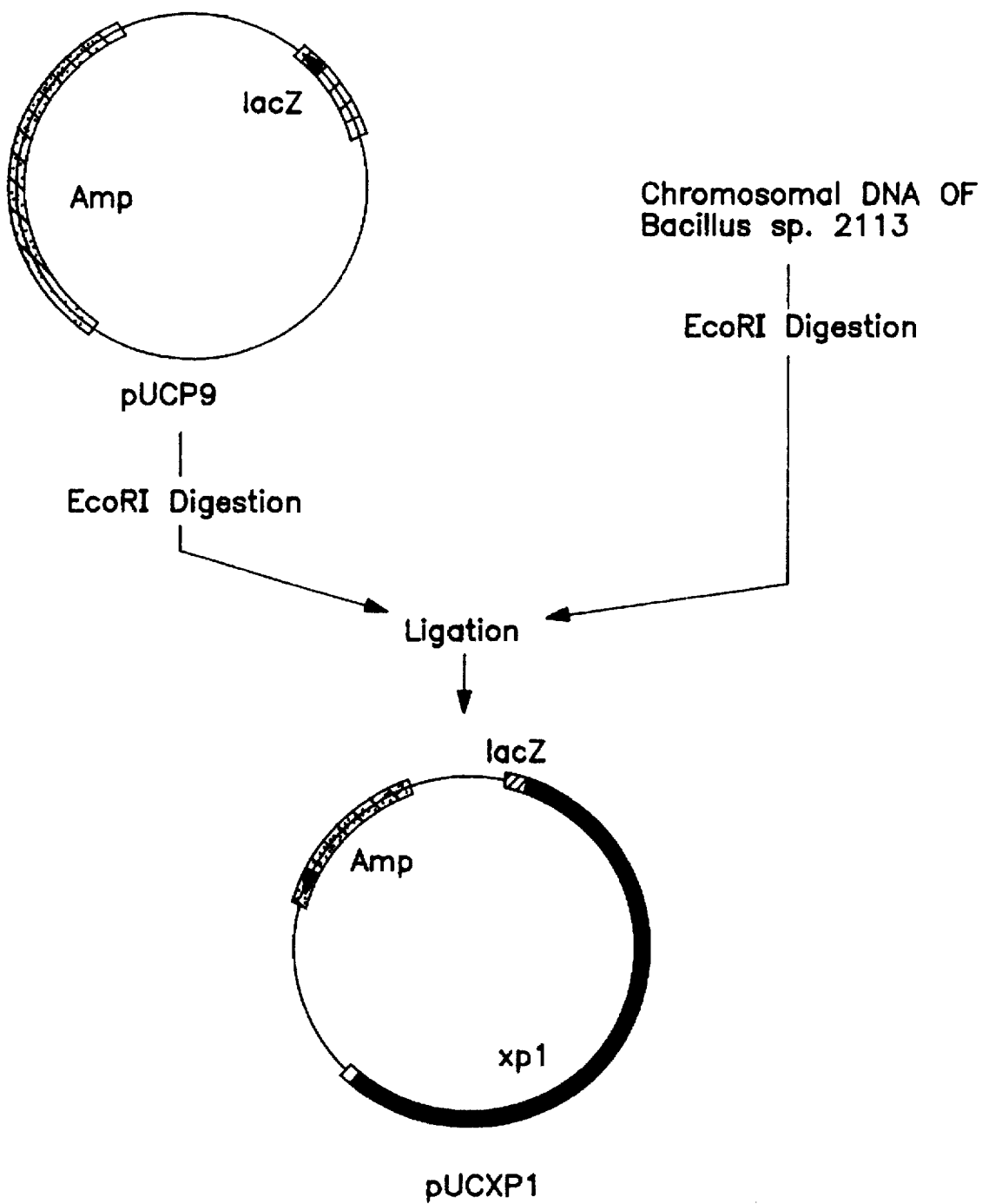
FIG. 7 is a schematic illustration of the construction of plasmid pUCXP1.

Further, FIG. 6 shows the restriction map of a DNA fragment containing the gene coding for xylanase XP1 obtained by the above-mentioned cloning.

The transformant *E. coli* JM109/pUCXP1 containing the xylanase XP1 gene has been deposited at the National Institute of Bioscience and Human-technology, Agency of Industrial Science and Technology, Ministry of International Trade and Industry under the Accession No. of FERM BP-5320.

(4) Determination of the N-Terminal Sequence of XP1

The N-terminal sequence of XP1 was determined by using as a sample an XP1 purified from a culture supernatant of *Bacillus sp.* 2113, and a protein sequencer (Model 477A, Applied Biosystems/Perkin Elmer) and a PTH analyzer (Model 120S, Applied Biosystems/Perkin Elmer). As a result, the N-terminal sequence of mature xylanase XP1 is as shown in SEQ ID NO: 3.

EXAMPLE 5

Production of a Recombinant Thermostable Xylanase

In this Example, recombinant thermostable xylanase XP1 was produced.

Plasmid pUCXP1 was completely digested with 500 ng of the EcoRI fragment of the gene of the invention obtained by EcoRI digestion and restriction enzyme EcoRI. Then, this plasmid was reacted with 1 µg of *E. coli/Bacillus subtilis* shuttle vector pHY3000PLK (Takara Shuzo) dephosphorylated by alkaline phosphatase (derived from calf intestine) and 2.5 U of T4 ligase in a ligation buffer at 16° C. for 2 hours, to thereby ligate the plasmid to the shuttle vector. *E. coli* JM109 was transformed with the resultant plasmid by the calcium chloride method.

The resultant transformant was inoculated in L medium (peptone 1%, yeast extract 0.5%, NaCl 0.5%, pH 7.0) containing 50µg/ml of tetracycline and incubated at 30° C. overnight.

Figure 8:
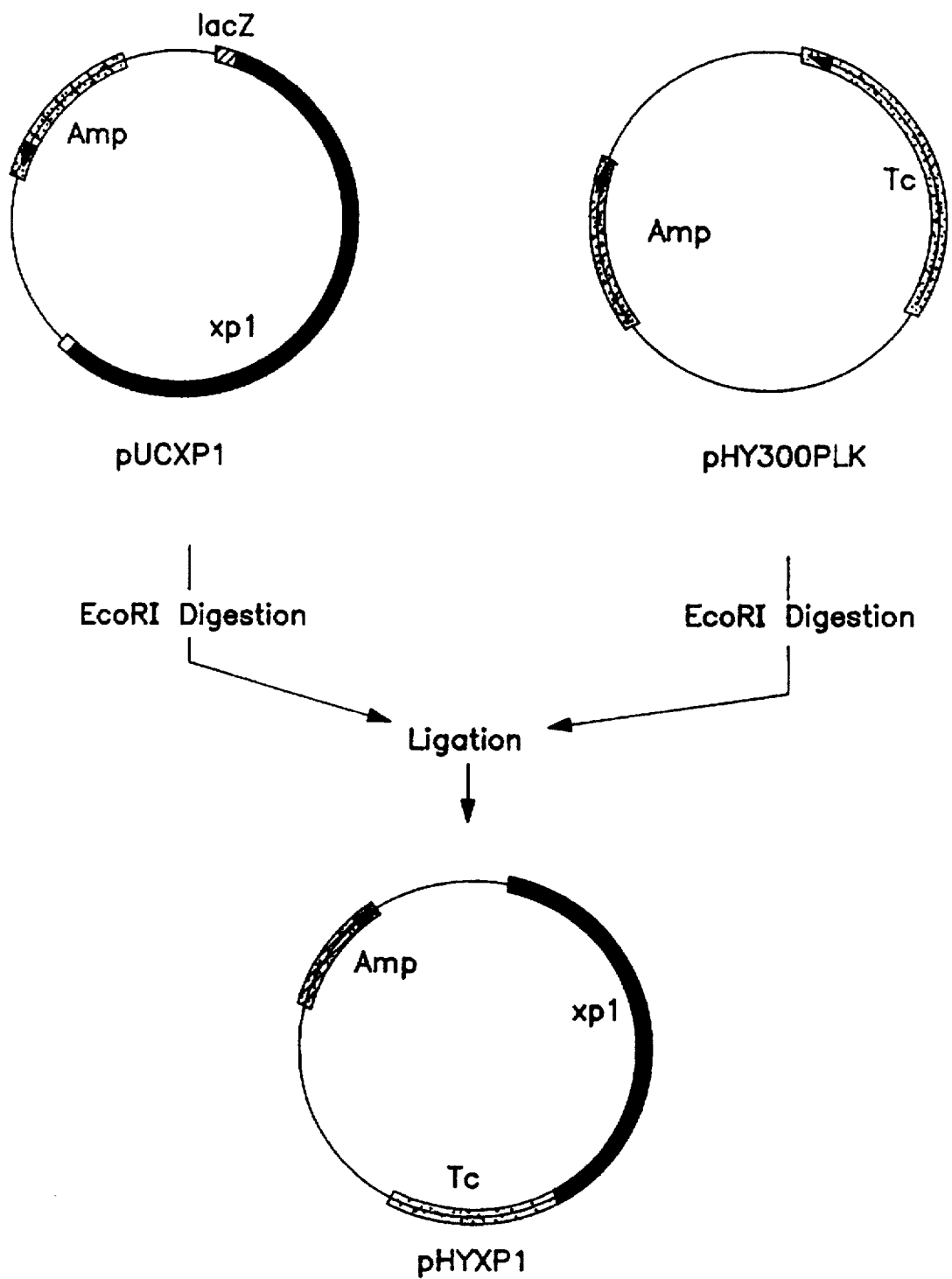
FIG. 8 is a schematic illustration of the construction of plasmid pHYXP1.

Plasmid DNA was prepared in large quantity from the thus obtained transformant by alkali extraction. This plasmid is designated as pHYXP1 and its construction is shown in FIG. 8.

*Bacillus subtilis* ISW1214 strain was transformed with the above-mentioned plasmid DNA by protoplast fusion. The resultant transformant was inoculated in 50 ml of a liquid xylan medium [0.6% birch xylan (Sigma), peptone 1%, yeast extract 0.5%, NaCl 10.5%, pH 7.0] containing 50 µg/ml of tetracycline in a 500 ml conical flask and cultivated at 37° C. for 3 days. After the cultivation, a culture supernatant was recovered by centrifugation (at 10,000 rpm for 10 min). The xylanase activity in the culture supernatant was 160 U/ml for 48 hours.

To the supernatant ammonium sulfate was added to 20–60% saturation. The resulting precipitate was collected by centrifugation (at 20,000 for 10 min) and dialyzed against 20 mM Tris-HCl (pH 7.2). The enzyme solution was charged onto CM Toyopearl 650-C (1.0 cm dia.×17 cm) equilibrated with 20 mM acetate buffer (pH 5.0).

The adsorbed fractions were eluted with a linear gradient of from 0 to 0.3M Nacl in 20 mM acetate buffer (pH 5.0) and fractionated by 1.5 ml.

Active fractions were pooled and subjected to SDS polyacrylamide gel electrophoresis. As a result, the purification was confirmed to be homogeneous. The enzyme had a molecular weight of approximately 22,500, an optimum pH for reaction of 5–8, a stable pH of 3–9 and an appropriate temperature range for action of 50°–80° C. Accordingly, it was concluded that this enzyme is XP1.

EXAMPLE 6

Bleaching of Pulp (1)

Two microliters per gram of pulp (bone dry weight) of the culture supernatant from *Bacillus sp.* 2113 in Example 1 above (containing 500 U/ml of thermostable xylanase) was added to hardwood, oxygen-bleached kraft pulp (Kappa number: 8.5, brightness: 46.0%). The consistency of the pulp was 3% and enzymatic treatment was carried out at pH 7.0, 70° C. for 2 hours. After the reaction, the pulp consistency was adjusted to 10% and the pulp was bleached by using chlorine, alkali, hypochlorites and chlorine dioxide in this order. A pulp treated the same way but without addition of the culture supernatant was used as a control bleached pulp. The standard conditions for bleaching are as follows.

Chlorine treatment: Chlorine is added at a rate of 1.6% in relation to the bone dry weight of pulp. Treatment is carried out at 40° C. for 30 minutes.

Alkali extraction: Alkali is added at a rate of 1.0% in relation to the bone dry weight of pulp. Treatment is carried out at 60° C. for 100 minutes.

Hypochlorite treatment: Hypochlorites are added at a rate of 0.5% in relation to the bone dry weight of pulp. Treatment is carried out at 45° C. for 120 minutes.

Chlorine dioxide treatment: Chlorine dioxide is added at a rate of 0.2% in relation to the bone dry weight of pulp. Treatment is carried out at 70° C. for 180 minutes.

In this Example, the bleaching of pulp was carried out with less chlorine, alkali or hypochlorites than used under the standard conditions. As a result, the amounts of chlorine and alkali necessary to achieve an equivalent brightness to that of the control bleached pulp (85.6%) could be reduced by 25%. As to chlorine dioxide, a 50% reduction was achieved.

Further, as a result of quantitative determination of AOX in waste water from bleaching with a halogen analyzer TOX-10 (Mitsubishi Chemical), it was found that AOX was reduced by 25% by the treatment with the culture supernatant.

The resulting reduction of bleaching chemical consumption, AOX and the like indicates that the bleaching efficiency on pulp was enhanced by the enzyme of the invention. Accordingly, the enzyme of the invention is useful in the bleaching of pulp from the view points of reducing the cost of chemicals and the organic chlorides.

EXAMPLE 7

Bleaching of Pulp (2)

Two microliters per gram of pulp (bone dry weight) of the culture supernatant from *Bacillus sp.* 208 in Example 2 above (containing 500 U/ml of thermostable xylanase) was added to hardwood, oxygen-bleached kraft pulp (Kappa number: 8.5, brightness: 46.0%). The consistency of the pulp was 3% and enzymatic treatment was carried out at pH 7.0, 70° C. for 2 hours. After the reaction, the pulp consistency was adjusted to 10% and the pulp was bleached by conventional methods using chlorine, alkali, hypochlorites and chlorine dioxide in this order. A pulp treated the same way but without addition of the culture supernatant was used as a control bleached pulp. The standard conditions for bleaching are as follows.

Chlorine treatment: Chlorine is added at a rate of 1.6% in relation to the bone dry weight of pulp. Treatment is carried out at 40° C. for 30 minutes.

Alkali extraction: Alkali is added at a rate of 1.0% in relation to the bone dry weight of pulp. Treatment is carried out at 60° C. for 100 minutes.

Hypochlorite treatment: Hypochlorites are added at a rate of 0.5% in relation to the bone dry weight of pulp. Treatment is carried out at 45° C. for 120 minutes.

Chlorine dioxide treatment: Chlorine dioxide is added at a rate of 0.2% in relation to the bone dry weight of pulp. Treatment is carried out at 70° C. for 180 minutes.

In this Example, the bleaching of pulp was carried out with less chlorine, alkali or hypochlorites than used under the standard conditions. As a result, the amounts of chlorine and alkali necessary to achieve an equivalent brightness to that of the control bleached pulp (85.6%) could be reduced by 27%. As to chlorine dioxide, a 53% reduction was achieved.

Further, as a result of quantitative determination of AOX in waste water from bleaching with a halogen analyzer TOX-10 (Mitsubishi Chemical), it was found that AOX was reduced by 28% by the treatment with the culture supernatant.

COMPARATIVE EXAMPLES 1–5

Bleaching of Pulp (Comparison with Commercial Enzymes)

Enzyme treatment and following pulp bleaching were carried out with various commercial enzymes and the reduction rates of chlorine, hypochlorites and AOX were compared with the results obtained in Examples 6 and 7. In Comparative Example 1, Irgazyme 40-X4 manufactured by Chiba-Geigy was used. In Comparative Example 2, Irgazyme 10A-X4 from the same manufacturer was used. In Comparative Example 3, Pulpzyme HC manufactured by Novo was used. In Comparative Example 4, Ecopulp manufactured by Alko was used. In Comparative Example 5, Cartazyme HS manufactured by Sandoz was used. Treatments similar to those carried out in Examples 6 and 7 were carried out using these enzymes. The results of Examples 6 and 7 and the results of each Comparative Example are shown in Table 6.

TABLE 6

| | Reduction Rate (%) | | |
|---|---|---|---|
| | Chlorine | Hypochlorites | AOX |
| Example 6 | 25 | 50 | 25 |
| Example 7 | 27 | 53 | 28 |
| Comparative Example 1 | 20 | 40 | 20 |
| Comparative Example 2 | 12 | 25 | 12 |
| Comparative Example 3 | 0 | 0 | 0 |
| Comparative Example 4 | 0 | 0 | 0 |
| Comparative Example 5 | 0 | 0 | 0 |

As seen from Table 6, the enzyme of the invention has higher reduction rates of chlorine, hypochlorites and AOX compared to conventional enzymes under the conditions of at pH 7.0 and 70° C. It should be noted that some enzymes exhibits almost no activity at such a high temperature. It has been demonstrated that the enzyme of the invention is excellent in thermostability.

EFFECT OF THE INVENTION

According to the present invention, there are provided novel thermostable xylanases and genes thereof, methods for producing such xylanases and their applications.

The present invention enables to produce a thermostable xylanase and thereby contributes to an industrial production of a thermostable xylanase. In addition, by treating pulp with the thermostable xylanase of the invention and/or a culture of the strain of the invention, bleaching efficiency on pulp can be enhanced. This contributes to reduce the amounts of bleaching chemicals in paper and pulp manufacturing as well as AOX levels in waste water.

What is claimed is:

1. A thermostable xylanase selected from thermostable xylanase XP1 or XP2 having the following physicochemical properties:

(1) Thermostable xylanase XP1 having the following physicochemical properties:
  i) Action: hydrolyzing the 1,4-β-D-xyloside bond of xylan to thereby produce reducing sugars of xylooligosaccharides.
  ii) Substrate specificity: acting on prepared xylans including birch xylan and oat spelt xylan, as well as xylan-containing materials including hardwood kraft pulp and oat spelt bran
  iii) Optimum pH and stable pH ranges: optimum pH for reaction ranging from 5 to 8 and the pH at which said xylanase is stable ranging from 3 to 9
  iv) Appropriate temperature range for action: 50° to 80° C.
  v) Thermostability: retaining about 90% or more enzyme activity after a 30 min treatment at 50° C. and exhibiting a residual activity of about 50% or more even after a 30 min treatment at 60° C.
  vi) Isoelectric point: around 8.1 vii) Molecular weight: approximately 22,500 as determined by SDS polyacrylamide gel electrophoresis viii) Inhibition: weakly inhibited by iodoacetic acid and EDTA and strongly inhibited by $Hg^{2+}$ and SDS (2) Thermostable xylanase XP2 having the following physicochemical properties:

i) Action: hydrolyzing the 1,4-β-D-xyloside bond of xylan to thereby produce reducing sugars of xylose and xylooligasaccharides ii) Substrate specificity: acting on prepared xylans including birch xylan and oat spelt xylan, as well as xylan-containing materials including hardwood kraft pulp and oat spelt bran iii) Optimum pH and stable pH ranges: optimum pH for reaction ranging from 5 to 8 and the pH at which said xylanase is stable ranging from 4.5 to 9 iv) Appropriate temperature range for action: 60° to 90° C.

v) Thermostability: exhibiting a residual activity of about 90% or more after a 30 min treatment at 70° C.

vi) Isoelectric point: around 8.5 vii) Molecular weight: approximately 32,000 as determined by SDS polyacrylamide gel electrophoresis viii) Inhibition: weakly inhibited by $Mn^{2+}$, $Co^{2+}$, $Cu^{2+}$, EDTA and iodoacetic acid and strongly inhibited by $Hg^{2+}$ and SDS.

2. A thermostable xylanase selected from recombinant thermostable xylanase XP1 or XP2 having the following physicochemical properties:

(1) Recombinant thermostable xylanase XP1 having the following physicochemical properties:

i) Action: hydrolyzing the 1,4-β-D-xyloside bond of xylan to thereby produce reducing sugars of xylooligosaccharides ii) Substrate specificity: acting on prepared xylans including birch xylan and oat spelt xylan, as well as xylan-containing materials including hardwood kraft pulp and oat spelt bran iii) Optimum pH and stable pH ranges: optimum pH for reaction ranging from 5 to 8 and the pH at which said xylanase is stable ranging from 3 to 9 iv) Appropriate temperature range for action: 50° to 80° C.

v) Thermostability: retaining about 90% or more enzyme activity after a 30 min treatment at 50° C. and exhibiting a residual activity of about 50% or more even after a 30 min treatment at 60° C.

vi) Isoelectric point: around 8.1 vii) Molecular weight: approximately 22,500 as determined by SDS polyacrylamide gel electrophoresis viii) Inhibition: weakly inhibited by iodoacetic acid and EDTA and strongly inhibited by $Hg^{2+}$ and SDS (2) Recombinant thermostable xylanase XP2 having the following physicochemical properties:

i) Action: hydrolyzing the 1,4-β-D-xyloside bond of xylan to thereby produce reducing sugars of xylose and xylooligosaccharides ii) Substrate specificity: acting on prepared xylans including birch xylan and oat spelt xylan, as well as xylan-containing materials including hardwood kraft pulp and oat spelt bran iii) Optimum pH and stable pH ranges: optimum pH for reaction ranging from 5 to 8 and the pH at which said xylanase is stable ranging from 4.5 to 9 iv) Appropriate temperature range for action: 60° to 90° C.

v) Thermostability: exhibiting a residual activity of about 90% or more after a 30 min treatment at 70° C.

vi) Isoelectric point: around 8.5 vii) Molecular weight: approximately 32,000 as determined by SDS polyacrylamide gel electrophoresis viii) Inhibition: weakly inhibited by $Mn^{2+}$, $Co^{2+}$, $Cu^{2+}$, EDTA and iodoacetic acid and strongly inhibited by $Hg^{2+}$ and SDS.

3. A recombinant thermostable xylanase containing the amino acid sequence represented by SEQ ID NO: 1.

4. A bleaching agent containing, as an active ingredient, thermostable xylanase XP1 or recombinant thermostable xylanase XP1 and/or thermostable xylanase XP2 or recombinant thermostable xylanase XP2 having the following physicochemical properties:

(1) Thermostable xylanase XP1 or recombinant thermostable xylanase XP1 having the following physicochemical properties:

i) Action: hydrolyzing the 1,4-62 -D-xyloside bond of xylan to thereby produce reducing sugars of xylooligosaccharides ii) Substrate specificity: acting on prepared xylans including birch xylan and oat spelt xylan, as well as xylan-containing materials including hardwood kraft pulp and oat spelt bran iii) Optimum pH and stable pH ranges: optimum pH for reaction ranging from 5 to 8 and the pH at which said xylanase is stable ranging from 3 to 9 iv) Appropriate temperature range for action: 50° to 80° C.

v) Thermostability: retaining about 90% or more enzyme activity after a 30 min treatment at 50° C. and exhibiting a residual activity of about 50% or more even after a 30 min treatment at 60° C.

vi) Isoelectric point: around 8.1 vii) Molecular weight: approximately 22,500 as determined by SDS polyacrylamide gel electrophoresis viii) Inhibition: weakly inhibited by iodoacetic acid and EDTA and strongly inhibited by $Hg^{2+}$ and SDS (2) Thermostable xylanase XP2 or recombinant thermostable xylanase XP2 having the following physicochemical properties:

i) Action: hydrolyzing the 1,4-β-D-xyloside bond of xylan to thereby produce reducing sugars of xylose and xylooligosaccharides.

ii) Substrate specificity: acting on prepared xylans including birch xylan and oat spelt xylan, as well as xylan-containing materials including hardwood kraft pulp and oat spelt bran iii) Optimum pH and stable pH ranges: optimum pH for reaction ranging from 5 to 8 and the pH at which said xylanase is stable ranging from 4.5 to 9 iv) Appropriate temperature range for action: 60° to 90° C.

v) Thermostability: exhibiting a residual activity of about 90% or more after a 30 min treatment at 70° C.

vi) Isoelectric point: around 8.5 vii) Molecular weight: approximately 32,000 as determined by SDS polyacrylamide gel electrophoresis viii) Inhibition: weakly inhibited by $Mn^{2+}$, $Co^{2+}$, $Cu^{2+}$, EDTA and iodoacetic acid and strongly inhibited by $Hg^{2+}$ and SDS.

5. A method for bleaching pulp, comprising contacting pulp to be bleached with the bleaching agent of claim 4, for a time sufficient to bleach the pulp.

6. A method for bleaching pulp, comprising carrying out a chemical bleaching and/or an alkali extraction before, after or during the contacting of pulp with the bleaching agent of claim 4.

* * * * *